(12) United States Patent
Batt

(10) Patent No.: US 10,668,762 B2
(45) Date of Patent: Jun. 2, 2020

(54) MULTI-TECHNOLOGY PRINTING SYSTEM

(71) Applicant: PHOTON JET LTD., Dn Har Hevron (IL)

(72) Inventor: Aryeh Batt, Dn Har Hevron (IL)

(73) Assignee: PRECISE BIO INC., Winston Salem, NC (US)

( * ) Notice: Subject to any disclaimer, the term of this patent is extended or adjusted under 35 U.S.C. 154(b) by 0 days.

(21) Appl. No.: 15/663,869

(22) Filed: Jul. 31, 2017

(65) Prior Publication Data
US 2018/0050550 A1 Feb. 22, 2018

Related U.S. Application Data

(60) Continuation-in-part of application No. 15/238,737, filed on Aug. 17, 2016, now Pat. No. 9,751,351, which is a division of application No. 14/365,119, filed as application No. PCT/IL2013/050845 on Oct. 21, 2013, now Pat. No. 9,446,618.

(30) Foreign Application Priority Data

Oct. 21, 2012 (IL) .......................... 222587
Oct. 21, 2012 (IL) .......................... 222588
Oct. 21, 2012 (IL) .......................... 222589

(51) Int. Cl.
B41M 5/40 (2006.01)
B41M 5/00 (2006.01)
(Continued)

(52) U.S. Cl.
CPC ............ *B41M 5/40* (2013.01); *B41M 5/0011* (2013.01); *B41M 5/42* (2013.01); *C23C 14/048* (2013.01);
(Continued)

(58) Field of Classification Search
CPC . B41J 2/035; B41J 2/06; B41J 2/14104; B41J 2/14314; B41J 2/065; B41J 2/04575;
(Continued)

(56) References Cited

U.S. PATENT DOCUMENTS 9,446,618 B2 9/2016 Batt
2009/0130427 A1 5/2009 Grigoropoulos et al.
2017/0043603 A1 2/2017 Batt

FOREIGN PATENT DOCUMENTS

WO WO-2011107599 A1 * 9/2011 ............ B01L 3/0268
WO 2012/136434 A2 11/2012
WO 2014/061024 A1 4/2014

OTHER PUBLICATIONS

IP.com search (Year: 2019).*
(Continued)

*Primary Examiner* — Lisa Solomon

(57) ABSTRACT

A system for performing substrateless and/or local donor Laser Induced Forward Transfer (LIFT), comprising a reservoir (9) comprising at least one opening and an energy source configured to deliver energy to a donor material within said reservoir, characterized by at least one of: said reservoir is embedded into a medical device; said reservoir is in fluid connection with a medical device; said reservoir is incorporated into a medical device; said reservoir contains at least one biologically active substance; and, said reservoir is in fluid connection with at least one source of at least one biologically active substance. This system enables deposition of material by LIFT without any need for a donor substrate. Methods of substrateless and local donor LIFT, in particular for medical and biological applications, are also disclosed.

61 Claims, 12 Drawing Sheets

(51) Int. Cl.
   *C23C 14/28* (2006.01)
   *C23C 14/04* (2006.01)
   *B41M 5/42* (2006.01)
   *B41J 2/14* (2006.01)

(52) U.S. Cl.
   CPC ..... *C23C 14/28* (2013.01); *B41J 2002/14322* (2013.01); *B41M 2205/08* (2013.01)

(58) Field of Classification Search
   CPC .... B41J 2/435; B41J 2/44; B41J 2002/14322; C23C 14/048; C23C 14/28; B41M 5/40; B41M 5/42; B41M 5/0011; B41M 2205/08
   See application file for complete search history.

(56) References Cited

OTHER PUBLICATIONS

Corresponding Israeli Patent Application No. 222587, filed Oct. 21, 2012.
Corresponding Israeli Patent Application No. 222588, filed Oct. 21, 2012.
Corresponding Israeli Patent Application No. 222589, filed Oct. 21, 2012.
Craig B. A. et al., "Laser Direct-Write Techniques for Printing of Complex Materials", Materials Research Society, MRS Bulletin, vol. 32, Jan. 2007, open access article: https://www.princeton.edu/~spikelab/papers/042.pdf.
Wust S. et al., "Controlled Positioning of Cells in Biomaterials—Approaches Towards 3D Tissue Printing", Journal of Functional Biomaterials, vol. 2, pp. 119-154, 2011.
Restriction Requirement Office Action issued by the U.S. Patent and Trademark Office dated Mar. 17, 2016, for U.S. Appl. No. 14/365,119.
Response filed on May 4, 2016 in reply to Restriction Requirement Office Action issued by the U.S. Patent and Trademark Office dated Mar. 17, 2016, for U.S. Appl. No. 14/365,119.
International Search Report for PCT/IL2013/050738, dated Jan. 26, 2014.
Written Opinion of the International Search Authority for PCT/IL2013/050738, dated Jan. 26, 2014.
International Preliminary Report on Patentability (Chapter I) for PCT/IL2013/050738, dated Apr. 21, 2015.

* cited by examiner

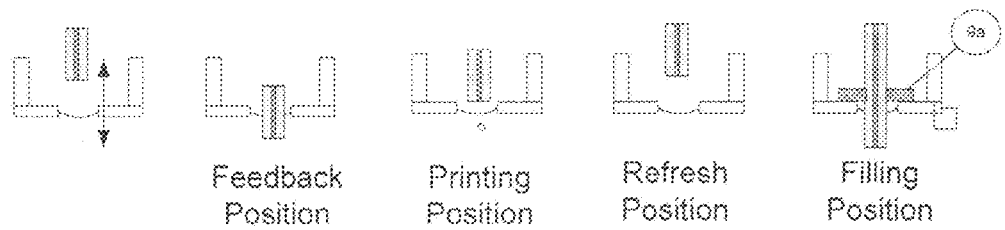
FIG. 6
FIG. 7B
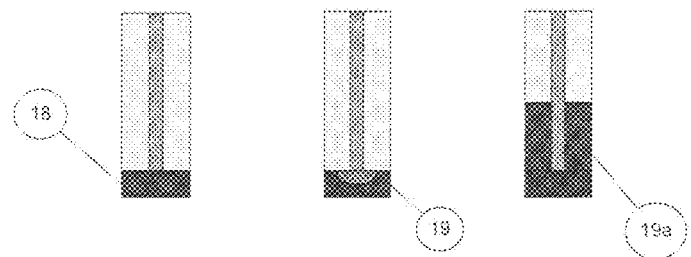
FIG. 7A          FIG. 7C
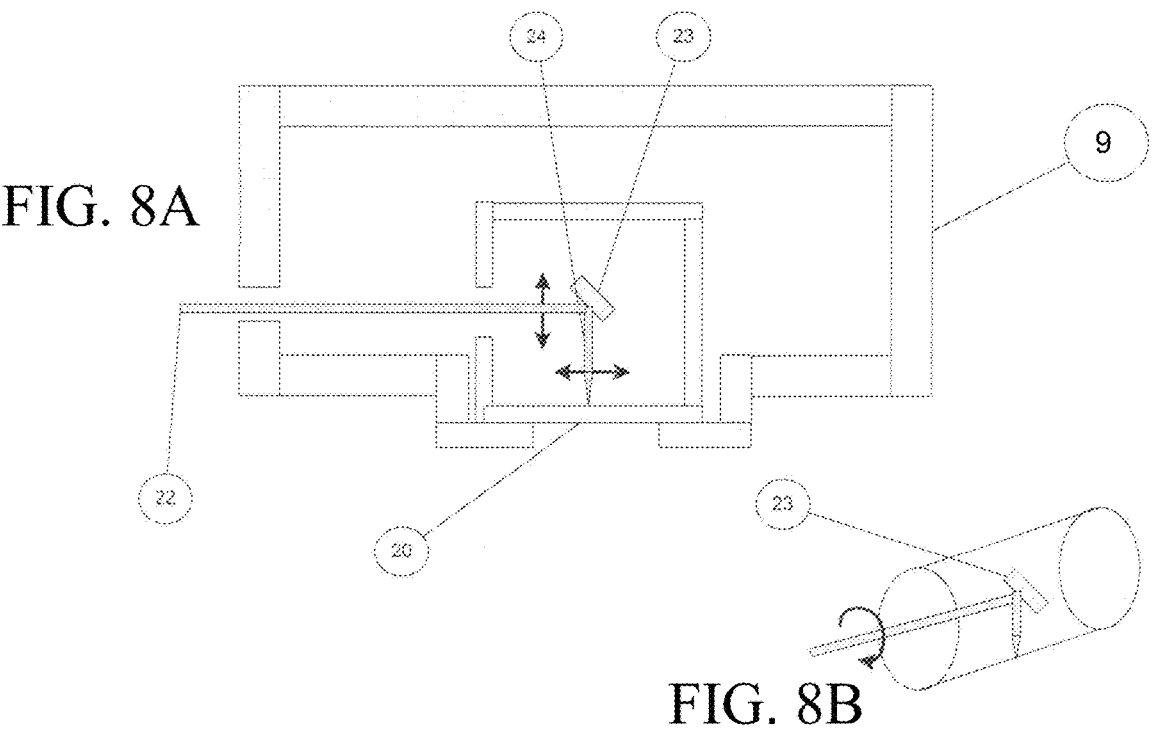
FIG. 8A
FIG. 8B Basic sequence #1

Basic sequence #2

Basic sequence #3

Basic sequence #4

MULTI-TECHNOLOGY PRINTING SYSTEM

CROSS REFERENCE TO RELATED PUBLICATIONS

This application is a Continuation-in-Part of U.S. patent application Ser. No. 15/238,737, filed 17 Aug. 2016, which is a divisional of U.S. patent application Ser. No. 14/365,119, filed 13 Jun. 2014 (U.S. Pat. No. 9,446,618, granted 20 Sep. 2016), which is a National Phase application of International (PCT) application No. PCT/IL2013/050845, filed 21 Oct. 2013, claiming priority from Israel Pat. Appl. Nos. 222587, 222588, and 222589, all of which were filed on 21 Oct. 2012. All of these applications are hereby incorporated by reference in their entirety.

FIELD OF THE INVENTION

This invention generally relates to material printing, material deposition, and material distribution. More specifically the invention relates to new methods of laser induced forward transfer for enabling 2D or 3D printing of various materials, distribution of a plurality of materials, high resolution patterning, and improved methods of medical treatment and intervention, particularly in endoscopic procedures.

BACKGROUND OF THE INVENTION

Conventional methods of printing as ink jet and screen printing have limitations of feature size and even more critical limitations of the kind of materials that can be printed in a repeatable, sustainable manner and with controlled quality.

There are many printing processes in the industry that are conducted over several sets of equipment thus limiting simplicity, accuracy, and quality of the printed platform. The integration between such systems is expensive from the aspect of resources and processes required to achieve adequate results.

Methods of LIFT are well known in research and in the industry. LIFT consists of a transparent substrate coated with a thin film of material to be transferred (the "donor"), which is facing a receiver substrate, (the "acceptor"). A laser pulse locally induces a thermal excitation that finally results in material transfer towards the acceptor.

The LIFT method can be used to transfer a rather large number of different materials, e.g. copper, nickel, aluminum, and chrome. In recent years laser transfer of liquid droplets was investigated both theoretically and experimentally with special emphasis on bio-materials. The main problem of LIFT technology, essentially used in academic research center, is the complexity of the LIFT system, including (i) the Laser manipulation; (ii) the donor holding and supplying. This invention overcome this inconvenience and complexity and brings LIFT means and method to industrial use.

Printing solutions and specifically industrial printing solutions are executed in many stages as material preparation, exposure and patterning, drying, sintering and other. In existing solutions these various activities are performed on various types of equipment in a production line. This invention further brings a comprehensive solution that equips several technologies built to be integrated on a single platform.

In medical devices, conventional systems for material application introduction and otherwise distribution, such as micropipettes have limitations of droplet size, and even more critical limitations of the kind of materials that can be distributed in a repeatable, sustainable manner and with a controlled quality and accuracy.

BRIEF SUMMARY OF THE CURRENT INVENTION

The current invention covers basic technology for printing, deposition and distribution of various materials, and a system perspective comprising these technologies in bringing a comprehensive solution for several applications. The basic applicable technologies to support the above are selected in a non-limiting manner from the group consisting of substrateless LIFT (SL-LIFT); Local Donor LIFT (LD-LIFT); new LIFT concepts; advanced sintering methods; and UV curing and feedback mechanisms.

The present invention also brings new means and methods of producing and utilizing a simple, accurate, precise and effective Substrate-Less LIFT and Local-Donor LIFT targeted, inter alia, as a medical device, avoiding the need of a substrate enabling distribution mechanism. The present invention discloses a system for performing substrateless and/or local donor Laser Induced Forward Transfer (LIFT), wherein said system comprises a reservoir (9) comprising at least one opening and an energy source configured to deliver energy to a donor material within said reservoir, thereby initiating a LIFT process. In preferred embodiments of the invention, the system is characterized in a manner selected from the group consisting of: said reservoir is embedded into a medical device; said reservoir is in fluid connection with a medical device; said reservoir is incorporated into a medical device; said reservoir contains at least one biologically active substance; and, said reservoir is in fluid connection with at least one source of at least one biologically active substance.

It is an object of this invention to disclose a system as defined above, wherein said reservoir comprises distributable material, and said system comprises: at least one tube filled with said material; a waveguide or other energy source which is submerged in the reservoir; a tube embedded in or onto said medical device; and a pulsed laser which generates said LIFT process in said medical device. In some preferred embodiments of the invention, said medical device comprises at least one illumination and acquisition fiber.

It is an object of this invention to disclose a system as defined in any of the above, wherein said reservoir is embedded into, in fluid connection with, or otherwise incorporated into a medical device. In some preferred embodiments of the invention, said system is configured to be used in a treatment protocol that comprises embedding a predefined material within or onto the body of a patient in need thereof. In some preferred embodiments of the invention, said system is configured to be utilizable without any necessity to prepare a substrate prior to distribution of said predetermined material. In some preferred embodiments of the invention, said predefined material comprises a biologically active substance. In some preferred embodiments of the system, said system is configured to dispose or embed a predefined material within or onto a cell, organ, tissue, or other biological structure. In some preferred embodiments of the system, said system is configured to be utilizable without any necessity to prepare a substrate prior to distribution of said predetermined material. In some preferred embodiments of the system, said predefined material comprises a biologically active substance.

It is an object of this invention to disclose a system as defined in any of the above, wherein said reservoir contains or is in fluid connection with at least one source of at least one biologically active substance.

The present invention discloses a printing, material deposition, and material distribution system, characterized by: one or more printing heads, each of which comprises at least one distributor that distributes material by substrateless LIFT (SL-LIFT) and/or Local Donor LIFT (LD-LIFT) method; one or more material reservoirs, each of which contains or in connection with at least one material to be fed by said printing head in a continuous manner; and one or more energy sources in connection with said one or more reservoirs; and at least one energy source is adapted to generate said LIFT process. The present invention further discloses a method of printing and material deposition by means of said system.

The present invention discloses a printing, material deposition, and material distribution system, as defined in any of the above, wherein laser operation parameters are selected from the group consisting of PW, PRF, power, pulse shape and other parameters can be controlled. The present invention further discloses a method of printing and material distributing by means of said system.

The present invention discloses a printing, material deposition, and material distribution system, as defined in any of the above, wherein the laser source is distributed to several waveguides submerged in the reservoir, and act each as an individual jetting apparatus.

The present invention discloses a printing, material deposition, and material distribution system, as defined in any of the above, wherein the laser is distributed by an energy distribution mechanism distributes the energy to at least one waveguide and at a time division or power division mechanism.

It is another object of the invention to disclose a continuous LIFT printing, material deposition, and material distribution system useful for high throughput, high resolution, printing of materials and distribution of materials, the system comprising: at least one reservoir of the printing material; a transparent substrate within said reservoir, said cylindrical is adapted to rotate in said reservoir; by means of said rotation, the cylinder is coated by the printed material; in the cylinder—a folding and a scanning mirror and optics that focus the energy on the substrate and in the position that the material is at the opening on the reservoir.

It is another object of the invention to disclose a continuous LIFT printing, material deposition, and material distribution system useful for high throughput, high resolution, printing of materials and distribution of materials, the system comprising: at least one reservoir of the printing material; at least one local donor within said reservoir.

It is another object of the invention to disclose a continuous LIFT printing, material deposition, and material distribution system as defined above, wherein the cylindrical element rotates and transfers through continues steps of the lift process, coating, energy pulse, jetting and recoating.

It is another object of the invention to disclose a continuous LIFT printing, material deposition, and material distribution system as defined above, wherein the system is operable in one or more of four modes of operation; namely, printing, filling, cleaning and patterning.

It is another object of the invention to disclose a continuous LIFT printing, material deposition, and material distribution system as defined above, wherein the laser parameters are selected from the group consisting of PW, PRF, power, and pulse shape.

It is another object of the invention to disclose a continuous LIFT printing, material deposition, and material distribution system as defined above, wherein the laser is distributed by an energy distribution mechanism which distribute the energy to at least one waveguide and at a time division or power division mechanism It is another object of the invention to disclose a continuous LIFT printing, material deposition, and material distribution system as defined above, wherein a sequence of pulses, PWs or PRRs is generated to receive adequate distributing parameters according to the application, material and process.

It is another object of the invention to disclose a continuous LIFT printing, material deposition, and material distribution system as defined above, wherein an intermediate plate of thermal conducting material is coated on the transparent cylinder.

It is another object of the invention to disclose a continuous LIFT printing, material deposition, and material distribution system as defined above, wherein an optical element, selected from the group consisting of lens, mirror, filter and scanning element is added at the end of the waveguide thereby improving energy distribution.

It is another object of the invention to disclose a continuous LIFT printing, material deposition, and material distribution system as defined above, wherein the waveguide has a graded index element that focuses and improve the beam quality in order to improve jetting quality.

It is another object of the invention to disclose a continuous LIFT printing, material deposition, and material distribution system as defined above, wherein the waveguide is a single mode fiber, a multimode fiber, or graded index fiber.

It is another object of the invention to disclose a continuous LIFT printing, material deposition, and material distribution system as defined above, wherein the reservoir walls are heated by an electrical current.

It is another object of the invention to disclose a continuous LIFT printing, material deposition, and material distribution system as defined above, wherein the reservoir is cooled by a cooling mechanism selected from the group consisting of thermo-electric cooler, heat pipes, and any mechanism useful to achieve longer shelve life of the material.

It is another object of the invention to disclose a continuous LIFT printing, material deposition, and material distribution system as defined above, wherein the material is heated by a heater selected from the group consisting of an energy source, CW laser, pulsed laser and any effective mechanism that heats the material locally in the reservoir.

The present invention discloses a printing, material deposition, and material distribution system, as defined in any of the above, wherein at least a portion of the walls of the reservoir and/or its opening is coated by a hydrophobic material, or is a wetted by a wetting layer, or treated by elevated or reduced temperature thereby surface shape parameters are controlled.

It is another object of the invention to disclose a continuous LIFT printing, material deposition, and material distribution system as defined above, wherein the system further comprising one or more of the following: multiple reservoirs; at least one waveguide in each reservoir; multiple energy sources; multiple central reservoirs with at least one material; a feedback, calibration and synchronization mechanism; and an adjustable mounting mechanism.

It is another object of the invention to disclose a continuous LIFT printing, material deposition, and material distribution system as defined above, wherein the feedback mechanism supports calibration, synchronization, alignment and process control of the system.

It is another object of the invention to disclose a continuous LIFT printing, material deposition, and material distribution system as defined above, wherein the alignment screws enable θy, θz and θx alignment.

It is another object of the invention to disclose a continuous LIFT printing, material deposition, and material distribution system as defined above, wherein the sensor acquires a printed target that has been printed on a different system or a target printed by this system in the same session.

It is another object of the invention to disclose a continuous LIFT printing, material deposition, and material distribution system as defined above, further comprising a sensor which measures the dimensions and other parameters of the printing and feedbacks to process control or to sintering or curing system.

It is another object of the invention to disclose a continuous LIFT printing, material deposition, and material distribution system as defined above, further comprising one or more energy sources, especially a pulsed laser distributed to one or more print-heads.

It is another object of the invention to disclose a continuous LIFT printing, material deposition, and material distribution system as defined above, further comprising one or more energy sources with an energy distribution mechanism that distributes the energy to one or more reservoirs; each source can be distributed to one or many reservoirs and the later can receive energy from other sources.

It is another object of the invention to disclose a continuous LIFT printing, material deposition, and material distribution system as defined above, wherein each reservoir or printing head may receive material from any of the material main reservoir sources.

It is another object of the invention to disclose a method as defined above, wherein the method further comprising a step of patterning the material; said patterning is selected from one or more members of the group consisting of trimming, disconnecting and otherwise changing the shape of jetted material.

It is another object of the invention to disclose a method as defined above, wherein the method further comprising a step of providing a feedback mechanism selected from the group consisting of a sensor, array of sensors, cameras, a source and detector, and any combination thereof.

It is another object of the invention to disclose a method as defined above, wherein the method further comprising a step of providing temperature regulation; temperature of the reservoir(s) is controlled by a heating mechanism and/or by a thermoelectric heater/cooler, thus receiving adequate material properties for printing, shelf life improvement and process stability.

It is another object of the invention to disclose a method as defined above, wherein the method further comprising a step of providing a cleaning mechanism, adapted to clean the said waveguides, or the said energy sources, thereby improving energy and printing efficiency and quality.

It is another object of the present invention to present a SL-LIFT and LD-LIFT printing, material deposition, and material distribution system comprising the following modules: (a) a LIFT-based depositing mechanism that which distributes or deposits materials without utilizing a substrate; (b) one or more reservoirs for various materials, each of said materials feeds the deposition head continuously, semi continuously or in a batch-wise manner; and (c) an energy source and means to introduce or otherwise apply energy produced by said energy source to the material in said reservoir, thereby generating the LIFT process.

It is another object of the present invention to present a SL-LIFT as defined above, wherein the energy source is selected in a non-limiting manner form a laser, an electric arc, a resistor element and any other pinpoint energy source.

It is another object of the present invention to present a SL-LIFT as defined in any of the above, wherein laser parameters, such as PW, PRF, power, pulse shape and other parameters are controllable.

It is another object of the present invention to present a SL-LIFT as defined in any of the above, additionally composing an energy distribution mechanism, which distribute the energy, e.g., the laser, to at least one waveguide at either mechanisms of time division or power division.

It is another object of the present invention to present a SL-LIFT as defined in any of the above, additionally comprising at least one arc receiver, wherein said at least one electric arc receiver which receives power from one or more signal generators. The parameters that control the production of said arc are selected in a non-limiting manner from the group consisting of power, such as energy parameters, pulse duration, pulse shape, pulse frequency and any combination thereof.

The present invention discloses a printing, material deposition, and material distribution system, as defined in any of the above, wherein at least one resisting element receives power from a signal generator that controls parameters of the power, said parameters are selected from the group consisting of energy, pulse duration and frequency.

It is another object of the invention to disclose a LIFT system as defined in any of the above, wherein a sequence selected from the group consisting of pulses, pulse widths, and PRRs is generated to receive adequate distributing parameters according to the application, material and process.

It is another object of the present invention to present a SL-LIFT as defined in any of the above, wherein the dimensions of the opening of the reservoir are fixable or adaptable and wherein the opening has an OPEN configuration and a CLOSED configuration and wherein said CLOSED configuration adapted to support the filling process.

It is another object of the present invention to present a SL-LIFT as defined in any of the above, wherein the opening of the reservoir can be closed to support the process of filling by an adjustable opening mechanism or by a plug connected to the energy element.

It is another object of the present invention to present a SL-LIFT as defined in any of the above, wherein at least one of the following is held true: (i) the reservoir is in thermal connection with a heating/cooling module; and (ii) the walls of the reservoir are heated/cooled by an electrical current to provide an adequate viscosity of the material in the reservoir.

It is another object of the present invention to present a SL-LIFT as defined in any of the above, wherein the material is heated by one or more members of the group consisting of thermo-electric coolers, Peltier module, heat pipes, CW laser, pulsed laser and any combination thereof.

It is another object of the present invention to present a SL-LIFT as defined in any of the above, wherein the opening of the reservoir or walls of the reservoir in connection with said opening are at least partially coated by one or more hydrophilic or hydrophobic materials, treated by wetting, maintained in a defined temperature or any combination thereof, thus controlling surface shape parameters.

It is another object of the present invention to present a continuous SL-LIFT adapted to provide high throughput, high resolution, sequenced deposition of materials.

It is another object of the present invention to present a continuous SL-LIFT as defined in any of the above, wherein said system comprises the following: (a) at least one reservoir comprising a distributable material; (b) at least one tube filled with said material; (c) a waveguide or other energy source which is submerged in the reservoir; (d) a tube adapted to be embedded in or onto a medical device, said medical device can comprise one or more illumination and acquisition fibers; and (e) pulsed laser which generates the LIFT process in said medical device.

It is another object of the present invention to present a continuous SL-LIFT as defined in any of the above, wherein the deposition is operated at a predefined rate over a predefined time span.

It is another object of the present invention to present a continuous SL-LIFT as defined in any of the above, wherein said system is operatable in one or more modes selected from the group consisting of a operation mode, deposition mode, filling mode, cleaning and patterning mode or any combination or sequence thereof.

It is another object of the present invention to present a continuous SL-LIFT as defined in any of the above, wherein the energy source is a laser.

It is another object of the present invention to present a continuous SL-LIFT as defined in any of the above, wherein the laser parameters are selected from the group consisting of PW, PRF, power, and pulse shape.

It is another object of the present invention to present a continuous SL-LIFT as defined in any of the above, wherein the laser is distributed by an energy distribution mechanism which distributes the energy to at least one waveguide, by means of either a time division or power division mechanisms.

It is another object of the present invention to present a continuous SL-LIFT as defined in any of the above, wherein the aforesaid sequence of pulses, PWs and PRRs are generated to receive adequate deposition parameters according to the application, material and process.

It is another object of the present invention to present a continuous SL-LIFT as defined in any of the above, wherein an intermediate plate, at least partially made or at least partially comprising one or more thermal conducting materials, is coated on, immersed, doped, or otherwise incorporated on or into the transparent cylinder.

It is another object of the present invention to present a continuous SL-LIFT as defined in any of the above, wherein an optical element, such as a lens, mirror, filter or a scanning element is either added to or connected with the end of the waveguide, thereby improving energy distribution.

It is another object of the present invention to present a continuous SL-LIFT as defined in any of the above, wherein the waveguide comprises a graded index element which focuses and/or improves the beam quality, thereby improving jetting quality.

It is another object of the present invention to present a continuous SL-LIFT as defined in any of the above, wherein the reservoir is cooled by a cooler selected from the group consisting of a thermo-electric cooler, Peltier module, heat pipes and any other cooling mechanism adapted to provide longer shelve life of the material.

It is another object of the present invention to present a continuous SL-LIFT as defined in any of the above, wherein the material is heated by an effective energy source, such as a CW laser, pulsed laser and any other mechanism that heats the material locally within the reservoir It is another object of the present invention to present a continuous SL-LIFT as defined in any of the above, wherein said system comprises a micro-tube LIFT distribution system, an illumination source (110) configured to emit light into a fiber or a fiber bundle and to illuminate an area to which material is to be deposited by said LIFT process, and a feedback mechanism comprising at least one sensor (111), all of which are embedded or otherwise incorporated into said medical device; further wherein said medical device is a tubular medical device comprising a micro-tube (109) disposed so as to distribute material transferred from said reservoir by said LIFT process. In some preferred embodiments, the system comprises: (a) an additional energy source (102a) configured to function as a feedback mechanism or a heating mechanism; and (b) a waveguide, one end of which is submerged in material stored in said reservoir disposed so as to transfer energy from said additional energy source to said material stored in said reservoir. In some preferred embodiments, wherein illumination source (110) is selected from the group consisting of LED, SLED, and laser diode.

It is another object of the present invention to present an SL-LIFT distribution or deposition head apparatus useful for material embedding in a medical device; wherein said SL-LIFT is as defined in any of the above; and wherein said integrated apparatus comprises (a) A set consisting of multiple reservoirs; (b) At least one waveguide located within or in communication with each reservoir; (c) Multiple energy sources; (d) Multiple central reservoirs with at least one material; (e) A feedback, calibration and synchronization mechanism.

It is another object of the present invention to present an SL-LIFT distribution or deposition head apparatus useful for material embedding in a medical device; wherein a feedback mechanism supports the calibration, synchronization, alignment and process control of the system.

It is another object of the present invention to present an SL-LIFT distribution or deposition head apparatus useful for material embedding in a medical device; wherein the sensor is adapted to both (i) acquire the target that the material has to be deposited on; and (ii) to receive a feedback after deposition.

It is another object of the present invention to present an SL-LIFT distribution or deposition head apparatus useful for material embedding in a medical device; additionally comprising at least one sensor which (i) measures the dimensions and distribution; and (ii) feedback input to a process control module.

It is another object of the present invention to present a medical device comprising a LIFT system adapted to embed a predefined material within or onto patient's body. In some preferred embodiments, the LIFT system is configured to be used in a treatment protocol that comprises disposing or embedding a predefined material within or onto the body of a patient in need thereof. In some preferred embodiments, the LIFT system is configured to dispose or embed a predefined material within or onto a cell, organ, tissue, or other biological structure. This LIFT system is utilizable without the necessity to prepare a substrate prior to distributing the material.

It is another object of the present invention to disclose a medical device comprising a system for performing substrateless and/or local donor Laser Induced Forward Transfer (LIFT), wherein said system comprises: a reservoir (9) comprising at least one opening, said reservoir embedded into, in fluid connection with, or incorporated into said medical device; and, an energy source configured to deliver energy to a donor material within said reservoir and thereby initiate a LIFT process.

In some preferred embodiments of the invention, said reservoir comprises distributable material, and said system comprises: at least one tube filled with said material; a waveguide or other energy source which is submerged in the reservoir; a tube embedded in or onto said medical device; and, a pulsed laser configured to generate said LIFT process in said medical device.

It is another object of the present invention to disclose a medical device as defined in any of the above, wherein said medical device comprises at least one illumination and acquisition fiber.

It is another object of the present invention to disclose a medical device as defined in any of the above, wherein said energy source comprises at least one source selected from the group consisting of a laser; a heating filament; an electric arc; and an electronic resistance mechanism. In some preferred embodiments of the invention, said energy source is a pulsed laser.

It is another object of the present invention to disclose a medical device as defined in any of the above, additionally comprising energy transfer means (8) for transferring energy from said energy source to a donor material within said reservoir. In some preferred embodiments of the invention, said energy source comprises a laser and said energy transfer means comprises a waveguide. In some preferred embodiments of the invention, said system comprises a waveguide positioning system selected from the group consisting of a piezoelectric system, a magnetic system, and a microelectromechanical system (MEMS).

It is another object of the present invention to disclose a medical device as defined in any of the above, wherein said system comprises at least one additional optical element in optical communication with a light beam passing through said waveguide. In some preferred embodiments of the invention, said additional optical element is selected from the group consisting of lenses, mirrors, filters, scanning elements, and optical coatings. In some preferred embodiments of the invention, said optical element is disposed at a distal end of said waveguide.

It is another object of the present invention to disclose a medical device as defined in any of the above, wherein said system comprises cleaning means for cleaning at least one of said waveguide and said energy source.

It is another object of the present invention to disclose a medical device as defined in any of the above, wherein said system comprises temperature regulating means for regulating temperature of material within said reservoir. In some preferred embodiments of the invention, said temperature regulating means are selected from the group consisting of an electric current passing through at least one wall of said reservoir; thermoelectric heater; thermoelectric cooler; Peltier module; irradiation by a CW laser; irradiation by a quasi-CW laser; irradiation by a pulsed laser; and heat pipes.

It is another object of the present invention to disclose a medical device as defined in any of the above, wherein said system comprises surface shape controlling means for controlling a surface shape of said material. In some preferred embodiments of the invention, said surface shape controlling means are selected from the group consisting of electrowetting, coating, heating of a reservoir wall surrounding said opening, and any combination thereof.

It is another object of the present invention to disclose a medical device as defined in any of the above, wherein said system comprises a plurality of energy sources.

It is another object of the present invention to disclose a medical device as defined in any of the above, wherein said system comprises a plurality of energy transfer means. In some preferred embodiments of the invention, the system additionally comprises a plurality of energy transfer means and energy distribution means for distributing output of said energy source among said plurality of energy transfer means.

It is another object of the present invention to disclose a medical device as defined in any of the above, wherein said system comprises adjustment means for adjusting the size of said opening.

It is another object of the present invention to disclose a medical device as defined in any of the above, wherein said system comprises preheating means for preheating material within said reservoir. In some preferred embodiments of the invention, said preheating means are selected from the group consisting of CW lasers and quasi-CW lasers.

It is another object of the present invention to disclose a medical device as defined in any of the above, wherein said system comprises a rotatable cylinder (20) disposed within said reservoir such that said rotatable cylinder is in contact with said donor material and such that energy from said energy source is deposited on an interior surface of said rotatable cylinder. In some preferred embodiments of the invention, said rotatable cylinder is transparent. In some preferred embodiments of the invention, said rotatable cylinder is translatable to a position that closes said opening. In some preferred embodiments of the invention, it additionally comprises a scanning mechanism (23), said scanning mechanism disposed to accept energy from said energy source to direct at least a portion of said energy to a predetermined spot on a surface of said cylinder. In some preferred embodiments of the invention, said scanning mechanism is selected from the group consisting of Galvo, MEMS, and micro mirrors. In some preferred embodiments of the invention, it comprises a folding and scanning mirror and focusing optics, said mirror and optics disposed within said cylinder so as to focus energy from said energy source onto a spot on a surface of said cylinder opposite to said opening. In some preferred embodiments of the invention, it additionally comprises an intermediate plate of thermally conducting material coated on said cylinder.

It is another object of the present invention to disclose a medical device as defined in any of the above, wherein said system comprises at least one printing head in fluid connection with said reservoir. In some preferred embodiments of the invention, said reservoir is disposed within said printing head. In some preferred embodiments of the invention, it additionally comprises a local energy source in each of said printing heads, said local energy source comprising a gain mechanism. In some preferred embodiments of the invention, it comprises a distributor configured to distribute material in a method selected from the group consisting of substrateless LIFT and local donor LIFT.

It is another object of the present invention to disclose a medical device as defined in any of the above, wherein said energy source is a pulsed laser, and additionally comprising laser parameter controlling means for controlling at least one laser parameter selected from the group consisting of pulse width, pulse repetition frequency, pulse power, and pulse shape.

It is another object of the present invention to disclose a medical device as defined in any of the above, wherein at least one selected from the group consisting of said energy distribution means and at least one of said energy transfer means is at least partially coated with a hydrophobic coating.

It is another object of the present invention to disclose a medical device as defined in any of the above, wherein at least one selected from the group consisting of said energy distribution means and at least one of said energy transfer means is at least partially coated with a hydrophilic coating.

It is another object of the present invention to disclose a medical device as defined in any of the above, wherein at least one selected from the group consisting of said energy distribution means and at least one of said energy transfer means is at least partially coated with a coating, and characterized by a predetermined hydrophobicity determined by at least one factor chosen from the group consisting of extent of coating with said coating and hydrophobicity of said coating.

It is another object of the present invention to disclose a medical device as defined in any of the above, additionally comprising an intermediate plate of thermally conductive material disposed at a distal end of said energy transfer means.

It is another object of the present invention to disclose a medical device as defined in any of the above, wherein said waveguide additionally comprises a graded index element.

It is another object of the present invention to disclose a medical device as defined in any of the above, wherein said system comprises flow means for providing a continuous flow of material through said reservoir.

It is another object of the present invention to disclose a medical device as defined in any of the above, wherein said system comprises a feedback mechanism that supports at least one of calibration, synchronization, alignment, and process control of said system. In some preferred embodiments of the invention, said feedback mechanism comprises at least one component selected from the group consisting of a sensor, array of sensors, cameras, a source and detector, and any combination thereof.

It is another object of the present invention to disclose a medical device as defined in any of the above, wherein said system comprises alignment screws disposed to provide $\theta_x$, $\theta_y$, and $\theta_z$ alignment.

It is another object of the present invention to disclose a medical device as defined in any of the above, wherein said system comprises a sensor that acquires a printed target that has been printed on a different system or a target printed by this system in the same session.

It is another object of the present invention to disclose a medical device as defined in any of the above, wherein said system comprises a sensor configured to measure at least one parameter of material printed by said system, and provides feedback to at least one system selected from the group consisting of process control, sintering, and curing.

It is another object of the present invention to disclose a medical device as defined in any of the above, wherein said reservoir is constructed of a material compatible with an acidic donor material.

It is another object of the present invention to disclose a medical device as defined in any of the above, wherein said medical device is configured to be used in a treatment protocol that comprises embedding a predefined material within or onto the body of a patient in need thereof. In some preferred embodiments of the invention, wherein said medical device is configured to be utilizable without any necessity to prepare a substrate prior to distribution of said predetermined material. In some preferred embodiments of the invention, said predefined material comprises a biologically active substance. In some preferred embodiments of the invention, said medical device is configured to dispose or embed a predefined material within or onto a cell, organ, tissue, or other biological structure. In some preferred embodiments of the invention, said medical device is configured to be utilizable without any necessity to prepare a substrate prior to distribution of said predetermined material. In some preferred embodiments of the invention, said predefined material comprises a biologically active substance.

It is another object of the present invention to disclose a medical device as defined in any of the above, wherein said reservoir contains or is in fluid connection with at least one source of at least one biologically active substance.

It is another object of the present invention to disclose a medical device as defined in any of the above, wherein: said medical device is a tubular medical device comprising a micro-tube (109) disposed so as to distribute material transferred from said reservoir by said LIFT process; said reservoir is embedded into, in fluid connection with, or otherwise incorporated to the medical device; and, said system comprises a micro-tube LIFT distribution system, an illumination source (110) configured to emit light into a fiber or a fiber bundle and to illuminate an area to which material is to be deposited by said LIFT process, and a feedback mechanism comprising at least one sensor (111), all of which are embedded or otherwise incorporated into said medical device. In some preferred embodiments of the invention, it comprises: an additional energy source (102*a*) configured to function as a feedback mechanism or a heating mechanism; and, a waveguide, one end of which is submerged in material stored in said reservoir disposed so as to transfer energy from said additional energy source to said material stored in said reservoir. In some preferred embodiments of the invention, said illumination source (110) is selected from the group consisting of LED, SLED, and laser diode.

It is an object of the present invention to disclose a LIFT method and systems comprised of a tube used as a reservoir of the required material an energy source as light source, laser, heating filament or other and a mechanism to bring the energy in to the tube at the required position.

It is an object of the present invention to disclose a LIFT method and systems wherein the energy required to displace the material from end of the tube can be energy distributed by a waveguide inserted in the tube at a precise distance from the surface.

It is an object of the present invention to disclose a LIFT method and systems wherein the waveguide is movable in the z-axis by a means selected from piezoelectric, magnetic, mechanic, and robotic mechanism, each of which is adapted to set the distance of the energy waveguide from the surface of the material with the ambient environment.

It is an object of the present invention to disclose a LIFT method and systems above wherein one or more waveguides or other energy mechanisms are translatable vertically in and out the reservoir thereby improving quality and stability of the distribution process.

It is an object of the present invention to disclose a LIFT method and systems above wherein one or many waveguides adapted to receive energy from several energy sources; said sources are regulated by parameters selected from a group consisting of a CW, pulsed laser, two or more pulsed lasers of equal or different operational parameters and any combination thereof.

It is an object of the present invention to disclose a LIFT method and systems above wherein the temperature of the material in the tube is controlled by a heating mechanism and or by a thermoelectric cooler, thereby receiving adequate material properties for deposition, shelf life improvement and process stability.

It is an object of the present invention to present a cleaning mechanism of the waveguide or energy source to improve energy and deposition efficiency and quality.

It is an object of the present invention to present a waveguide with one or more members of the group consisting of optics, lenses, mirrors, coatings and any optical element adapted to improve distribution quality accuracy, throughput and any other distribution parameters.

It is an object of the present invention to present a preventive mechanism selected from the group consisting of coating, wetting, rotation, movement on and of the waveguide, and any other energy source adapted to improve energy and deposition efficiency and quality.

It is an object of the present invention to present an LIFT method and system with a tube adapted to be filled with a material in a manner that there is no need to disassemble or remove distributing head.

It is an object of the present invention to present an LIFT method and system comprising one or more reservoirs that are fed by either a central reservoir or a plurality of reservoirs with one or more different materials.

It is an object the present invention to present a LIFT method and system with feedback and control based on illumination; the system comprises one or more sensors targeted on the point of distribution or a feedback received from the laser source.

It is an object the present invention to present method producing a SL-LIFT system, said method comprising steps of: providing a SL-LIFT or LD-LIFT deposition head; integrating therein one or more reservoirs for various materials; providing each of said materials in solid or liquid connection with said deposition head; integrating an energy source therein; and providing energy transfer means for applying energy to said material in said reservoir thereby generating a LIFT process. In some embodiments, the method additionally comprises providing at least one tube adapted to be embedded in or onto a medical device; and filling said at least one tube with said material.

It is an object of the present invention to disclose a method of LIFT-based bio-printing, comprising: (a) introducing a quantity of a biological material into a reservoir comprising at least one opening; (b) placing an acceptor substrate opposite to said opening; (c) providing an energy source disposed to provide energy to said biological material; (d) applying at least one pulse of energy from said energy source to said biological material, thereby providing local heating to said biological material sufficient to create a bubble within said biological material and thereby forcing a portion of said biological material from said reservoir via said opening onto said acceptor substrate; (e) repeating the previous step until a bio-printed material of a predetermined structure and shape is obtained; (f) consolidating and stiffening said bio-printed material; and, (g) allowing said bio-printed material to mature.

It is a further object of the present invention to disclose a method of LIFT-based bio-printing as defined above, wherein said method does not comprise any step involving the use of a donor substrate.

It is a further object of the present invention to disclose a method of LIFT-based bio-printing as defined in any of the above, comprising replenishing said biological material from a material feeder in fluid connection with said reservoir.

It is a further object of the present invention to disclose a method of LIFT-based bio-printing as defined in any of the above, wherein said step of introducing a quantity of a biological material into a reservoir comprising at least one opening comprises introducing a plurality of biological materials from a plurality of reservoirs.

It is a further object of the present invention to disclose a method of LIFT-based bio-printing as defined in any of the above, additionally comprising providing at least one printing head in fluid connection with said reservoir. In some preferred embodiments of the invention, said step of providing at least one printing head comprises incorporating said reservoir into said printing head.

It is a further object of the present invention to disclose a method of LIFT-based bio-printing as defined in any of the above, wherein said step of applying at least one pulse of energy from said energy source to said biological material comprises applying at least one pulse of energy so as to provide droplets having the size of a single cell.

It is a further object of the present invention to disclose a method of LIFT-based bio-printing as defined in any of the above, wherein said step of consolidating and stiffening comprises at least one technique selected from the group consisting of irradiation with visible light, irradiation with UV light, and heating.

It is a further object of the present invention to disclose a method of LIFT-based bio-printing as defined in any of the above, comprising continuously flowing said biological material through said reservoir.

It is a further object of the present invention to disclose a method of LIFT-based bio-printing as defined in any of the above, wherein said biological material is selected from the group consisting of bio-polymers, cells, cell culture media, soluble sacrificial materials, extra-cellular materials, growth factors, and scaffolding materials.

It is a further object of the present invention to disclose a method of LIFT-based bio-printing as defined in any of the above, wherein said biological material comprises cells, said cells are bio-printed along with ink, and said step of forcing a portion of said biological material from said reservoir via said opening onto said acceptor substrate comprises depositing said cells in positions so as to create functioning tissue. In some preferred embodiments of the method, said functioning tissue is selected from the group consisting of vascular tissue, nerve tissue, skin tissue, ocular tissue, liver tissue, kidney tissue, bone, and cartilage. In some preferred embodiments of the method, said step of forcing a portion of said biological material from said reservoir via said opening onto said acceptor substrate comprises depositing non-cellular biological material followed by at least one step of depositing cells. In some preferred embodiments of the method, it comprises depositing a plurality of biological materials in separate steps.

It is a further object of the present invention to disclose a method of LIFT-based bio-printing as defined in any of the above, performed on the system as defined in any of the above.

BRIEF DESCRIPTION OF THE DRAWINGS

In order to better understand the invention and its implementation in practice, a plurality of embodiments will now be described, by way of non-limiting example only, with reference to accompanying drawings:

FIG. 6 schematically illustrates a method of a high speed printing process according to the invention herein disclosed in which a waveguide is translated vertically during the course of the process;

FIGS. 7A-7C schematically illustrate several embodiments of the invention that comprise add-ons to the waveguide and different types of waveguides, namely, a local intermediate layer (FIG. 7A), a waveguide to which a lens has been added (FIG. 7B), and a waveguide tip to which Graded Index material has been added (FIG. 7C);

FIGS. 8A and 8B schematically illustrate an overall view and a close-up view, respectively, of a non-limiting embodiment of the system herein disclosed, in which the system comprises a rotating cylinder;

FIGS. 19A-19C schematically illustrate several aspects of the local-donor LIFT concept, in which FIG. 19A illustrates schematically a standard LIFT process, FIG. 19B illustrates schematically a theoretical limiting case in which only that part of the substrate and donor material heated by the laser remain, and FIG. 19C illustrates a non-limiting embodiment of the invention in which donor material is embedded in or is part of the reservoir and flows through it; and, FIG. 20 schematically illustrates a micro-tube LIFT system.

DETAILED DESCRIPTION OF THE PREFERRED EMBODIMENTS

Figure 1:
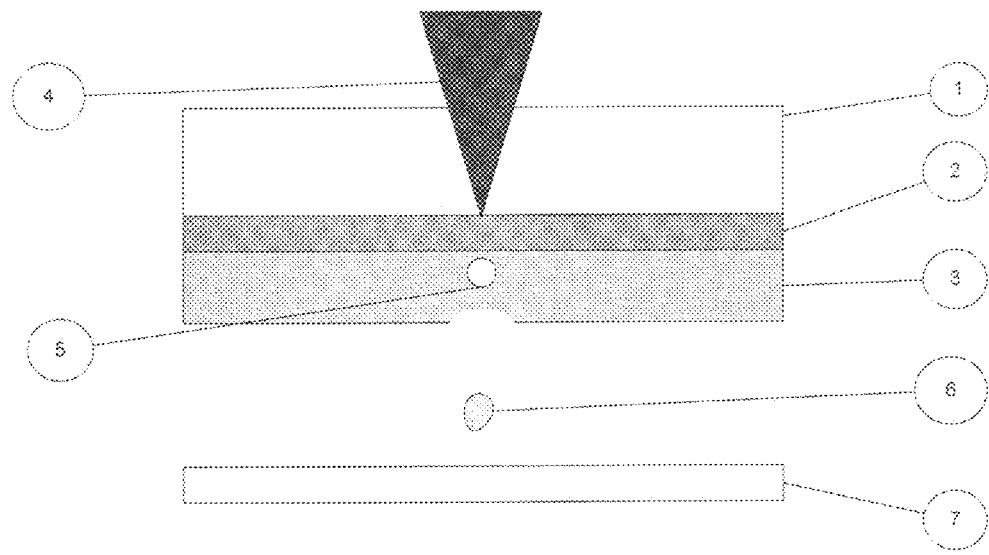
FIG. 1 schematically illustrates the conventional LIFT process known in the prior art.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification and examples, but only as indicated in the accompanying claims, with the proper scope determined only by the broadest interpretation of said claims.

The recitation of particular combinations of elements of the system disclosed herein or of particular combinations of steps of the method herein is not intended to limit the invention to those combinations. All non-self-contradictory combinations of elements disclosed herein and all non-self-contradictory combinations of method steps disclosed herein are considered by the inventors to be within the scope of the invention.

The following abbreviations are used herein. "PW" is used to represent "pulse width"; "PRR" is used to represent "pulse repetition rate"; "PRF" is used to represent "pulse repetition frequency"; "LIFT" is used to represent "laser-induced forward transfer"; "LD-LIFT" is used to represent "local donor laser-induced forward transfer"; and "SL-LIFT" is used to represent "substrateless laser-induced forward transfer."

The term "calibration" is used herein to refer to the accuracy and orientation of the head in the system; and to the calibration of head parameters such as laser power, laser PW, laser PRF, heating and cooling temperatures, speed of movement of the waveguide, etc.

The term "medical device" is used herein to refer to any instrument, apparatus, implant, or other similar or related article that is intended for use in the diagnosis of disease or other conditions, or in the cure, mitigation, treatment, or prevention of disease, or intended to affect the structure or any function of the body and which does not achieve any of its primary intended purposes through chemical action within or on the body or by being metabolized. Non-limiting examples of "medical devices" according to this definition include devices such as endoscopes and laparoscopes; pipettes and micropipettes; catheters; infusion equipment; recycling systems for biological fluids; implanted feeding tubes; irrigators; delivery systems for drugs, medicaments, biological molecules, nutrients, inorganic compounds, etc.; implantable pumps and tubing thereof; intradural drug injection and feeding systems; in situ delivery modules for neurological drugs and neurotransmitters; etc.

The term "biologically active substance" is used herein to refer to any substance or composition, whether derived naturally or produced synthetically, that is found in viruses, cells, or biological tissue; any substance or composition, whether derived naturally or produced synthetically, that is derived from such a substance or composition; any drug, medication, physiologically active substance or composition, or physiologically inert substance or composition that can bind to, be absorbed by, be adsorbed on, be injected into, or chemically react with at least one of viruses, cells, organs, tissues, or portions thereof; any drug, medication, physiologically active substance or composition, or physiologically inert substance or composition that can affect any chemical or biological reaction pathway or be used as a marker for at least one chemical or biological reaction pathway. Non-limiting examples of "biologically active substances" according to this definition include in vitro reagents; markers and biomarkers and derivatives thereof; contrast agents; drugs; medications; naturally-occurring biological fluids; etc.

In addition to the invention of the single head substrateless waveguide LIFT, two additional system concepts are provided for methods and systems for printing. The first of these relates to a multi-head device where the device comprises a plurality of heads; in some embodiments, these systems comprise a plurality of multi-head devices. The second concept is a system that combines at least two of the four basic technologies defined above, integrating them into a single apparatus. This integrated technology provides a single comprehensive solution for processes that in require several independent machines in the printing methods known in the art.

In one embodiment of the invention, a system is disclosed in which one or more materials are jetted onto the required substrate at specific dimensions. If required, excess material can be removed, textured, processed or patterned to a predefined size and shape utilizing predefined retrievable data. In another embodiment of the invention, a method of jetting and processing the material is disclosed.

According to another embodiment of the invention, a system is disclosed, wherein other treatments to the material is activated by e.g., the third or fourth component of the combined head, thus completing a full printing process.

It is within the scope of the invention to disclose a system and method of swapping. The term "swapping" refers herein to selecting one sequence of operation steps from two or more different sequences of steps.

It is within the scope of the invention to disclose a printing system based on SL-LIFT and/or LD LIFT and/or LIFT that can be used as a sintering and/or drying system with a laser-based sintering head and/or a curing head.

A printing system based on SL-LIFT and/or LD LIFT and/or LIFT is disclosed that combines or integrates two or more technologies selected, in a non-limiting manner, from patterning, curing and sintering. The technologies may be used together in any sequence. In some embodiments, the system additionally comprises a feedback mechanism. In some embodiments, the feedback mechanism comprises technologies such as a sensor, array of sensors, cameras, a source and detector; any other feedback mechanism(s) known in the art may be used. In some embodiments, the system additionally comprises methods for one or more of calibrating, registering and synchronizing.

The printing system herein disclosed can be used for any printing technologies known in the art. Non-limiting examples include inkjet, screen printing, or exposure based patterning systems.

In some embodiments, the system comprises (i) at least one reservoir, at least one of said reservoirs at least partially filled by a material, (ii) at least one energy source, said light source is selected in a non-limiting manner form one or more members of a group consisting of: one or more lasers; one or more heating filaments; any other suitable mechanism and applicable means adapted to bring a required energy into said reservoir at a required location; and any combination thereof.

In some embodiments, multiple independent energy sources are used. In preferred embodiments, these energy sources are selected from the group consisting of continuous wave (CW) lasers; and pulsed lasers. In other embodiments, the multiple independent energy sources may also comprise a local low-power laser for each printing head, each laser comprising a gain mechanism such as a ytterbium fiber.

In some embodiments, the temperature of the reservoir(s) is controlled by a heating mechanism and/or by a thermoelectric heater/cooler, thus improving the donor material's properties for printing, shelf life, and/or stability.

In some embodiments, the system further comprises at least one waveguide with additional optics such as lenses, mirrors, coatings, or other optical elements.

In some embodiments, the system further comprises a reservoir that can be filled in such way as to reduce or eliminate any need to disassemble or remove the printing head.

In some embodiments, the system comprises a plurality of reservoirs. The plurality of reservoirs may be a multi compartment reservoir; a plurality of independent reservoirs; or a sequence or train of reservoirs in fluid connection and fed by one or more central reservoirs. In some embodiments, the plurality of reservoirs are in fluid connection with one or more printing heads.

A comprehensive printing solution head is presented herein. The head is adapted to be mounted on a system in the same manner that an inkjet printing head is integrated in a printing system. The multi-technology printing head is integrated in a system with accessories as lasers, material reservoirs, control and electronics systems, adjustable mechanical interface and other accessories needed to operate the system's technology heads. The multi-technology head software interfaces by a predefined interface control document (ICD) to the platform's software. The control is a part of operating system and calibration and maintenance system. Hence for example, the control mechanism is adapted to be responsible for scanning modules in the patterning head and sintering head; and is set to operate in synchronization with the jetting head according to the aforesaid calibration. In some embodiments, the multi-technology head includes an SL LIFT and/or LD LIFT head with one or more of the following: another SL LIFT head, sintering head, patterning head, an UV curing head and any combination thereof.

The systems and methods in the present invention are based on the physical phenomena of standard LIFT material distribution. Reference is now made to FIG. 1, illustrating schematically the LIFT process as it is known in the prior art: a transparent substrate (1) is coated with a thin film of the transferred material (3, the "donor"). A layer of donor material 3 faces the receiver substrate (7, the "acceptor"). There may be an intermediate layer between the substrate and donor layers. A laser pulse (4) induces a local thermal excitation that results in rapid heat transfer to the donor material, generating a gas bubble (5) at the predefined focus point. The gas bubble rapidly travels to the surface and injects a droplet (6) from the boundary between the donor material and the ambient environment to the surface of the acceptor.

Figures 2A, 2B:
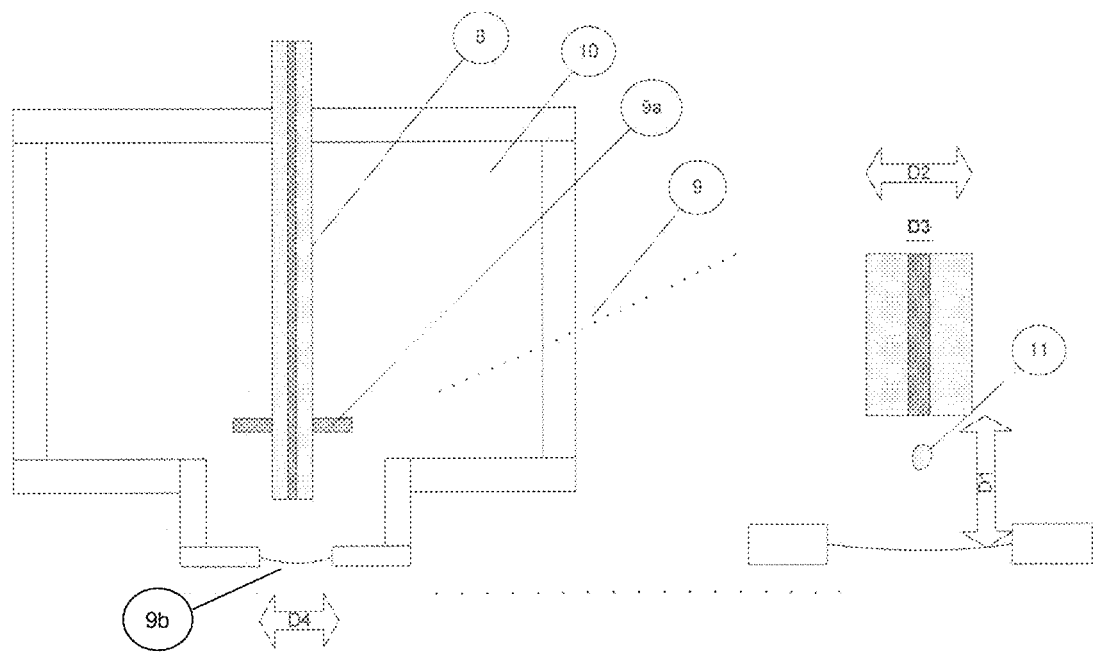
FIGS. 2A and 2B schematically illustrate general and close-up views, respectively, of a substrateless LIFT (SL-LIFT) system according to one embodiment of the invention herein disclosed.

Reference is now made to FIG. 2, which illustrates schematically (not to scale) one embodiment of the improved LIFT system disclosed in the present invention. Unlike LIFT systems and methods known in the art, in the present invention, the donor material itself is used as the donor substrate. FIG. 2A provides a general illustration of the system. A reservoir (9) contains the donor material (10). An energy source or means for transferring energy from an energy source is disposed so as to be able to transfer energy to the donor material within the reservoir. In the embodiment shown in FIG. 2, the energy source is a laser external to the reservoir, the light from which is transferred to the donor material via an energy transfer means such as a waveguide (8). Any other appropriate energy source known in the art can be used, however. Non-limiting examples of energy sources used in embodiments of the invention not illustrated in FIG. 2 include an electric arc or electronic resistance mechanism. The reservoir comprises at least one opening 9*b* that enables material to exit. While the size of the opening is not critical to the operation of the system, in typical embodiments, it much larger than nozzles in typical inkjet printing heads. The increased size of the opening relative to those typically found in inkjet printing heads enables flow of large particles and of viscous materials without clogging the system. In preferred embodiments, the opening's largest dimension D4 (or diameter in embodiments in which it is circular) is at least 100 μm, and may range up to several mm. In order to enable refilling of the reservoir without loss of material during the refilling, in preferred embodiments, the reservoir is provided with a stopper 9a.

In some embodiments of the invention, one or more heating and/or cooling mechanisms are in thermal connection with the reservoir. The viscosity of the material is controlled via heating of the material, while cooling can improve the shelf life of the material. In preferred embodiments of the invention, the heating mechanism is selected from the group consisting of resistive heating by at least one electrical filament, laser energy, and resistive heating from electrical current flowing through the reservoir walls; any other heating mechanism known in the art may be used as well. In preferred embodiments of the invention, the cooling mechanism is selected from the group consisting of thermoelectric coolers such as a Peltier module, heat pipes, and fluid flowing through the reservoir walls; any other cooling mechanism known in the art may be used as well.

The reservoir may be constructed from any of a variety of materials. Non-limiting examples of suitable materials for construction of the reservoir include plastics such as poly- and oligo-carbonates, metals and metal-containing compositions; and organic and inorganic compositions. Materials such as plastics that enable printing of acid materials are used in preferred embodiments.

The size of the opening of the reservoir (D4) can be adjustable or fixed. Adjustment of the opening of the reservoir enables control of the meniscus curvature in relation to the type of material, viscosity and required printing parameters. In some embodiments, control of the meniscus curvature is achieved by electro-wetting of the walls, heating of the material, heating or coating the walls of the opening, or a combination thereof. Control of the meniscus curvature is essential in order to receive uniform droplet properties from each energy source. In some embodiments of the invention, a vacuum or partial vacuum in the reservoir controls the boundary of the surface with the ambient environment.

Reference is now made to FIG. 2B, which provides a close-up (not to scale) view of the LIFT process as it is performed in the novel system of the present invention. The distal end of the energy source is placed at a distance D1 from the reservoir opening; in general, the energy source will be submerged in the donor material. D2 represents the overall width of the energy source, while D3 the width of the core (active area, e.g. the waveguide in cases in which the energy source is a laser). Upon application of energy, a gas bubble 11 is generated in the donor material. If a receiver substrate is placed facing opening 9b, an SL-LIFT process will occur in which the energy source in the reservoir acts as the donor substrate, without any necessity for a separate donor substrate.

The parameters of the energy applied to the donor material are controllable by a central mechanism, such as a laser with controllable PRR, PW, power, and rise time, an electrical pulse generator connected to the arc, and/or a resistance element. These embodiments can comprise one or more additional or alternative energy sources, such as a CW laser, electronic heater element, or any other heating module known in the art, that heat the material and thus modify its viscosity to a value adequate for the required printing parameters. In addition to control of the energy and viscosity, control of D1, the distance between the end of the energy source and the surface of the material, adds degrees of freedom setting droplet size and frequency of the process.

Figure 3:
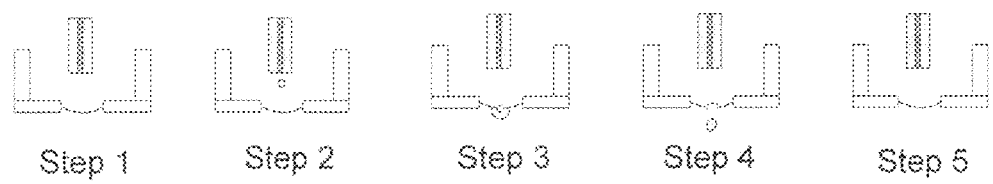
FIG. 3 schematically illustrates one embodiment of a five step SL-LIFT method.

Reference is now made to FIG. 3, illustrating in a non-limiting manner and not to scale a one embodiment of an SL-LIFT process that can be performed using the system disclosed herein. The process illustrated in FIG. 3 is referred to herein as the "five step SL-LIFT process." In step 1, a pulse of energy is applied from the energy source, causing a gas bubble to form (step 2). In step 3, the gas bubble forces donor material toward the reservoir opening 9b. Jetting, i.e. the bubble and donor material exit the reservoir and encounter the receiver substrate, occurs in step 4. Finally, in step 5, donor material from within the reservoir refreshes the interface. The frequency with which these steps can be repeated in a system comprising a single energy transfer means (e.g. a single waveguide) will depend on the system refresh time, which depends on the properties of the material (e.g. viscosity, surface tension, etc.) and on the waveguide parameters (D1, D3).

Figure 4:
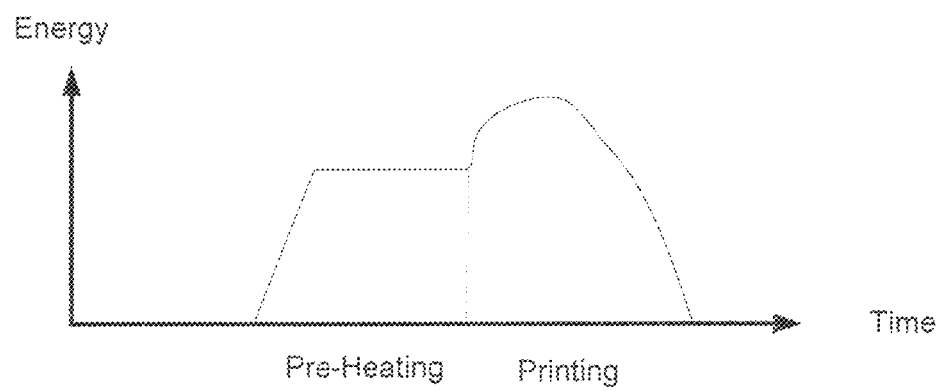
FIG. 4 schematically illustrates a non-limiting example of an energy profile provided by an energy source during the course of an SL-LIFT process according to one embodiment of the invention herein disclosed.

Reference is now made to FIG. 4, illustrating a qualitative energy profile for the deposition of energy as a function of time during one embodiment of an SL-LIFT process performed by using one embodiment of the system disclosed herein. As shown in the figure, it is possible to decrease the refresh time by preheating the material prior to application of the pulsed laser energy, by application of a heat source such as a continuous wave (CW) laser or quasi-CW laser, in order to provide local heating of the material before pulse energy required for the SL-LIFT process itself. In this way one can produce a local reduction in the viscosity and the surface tension of the donor material before the jetting. This SL-LIFT process leads to a decreased refresh time of the material and an increased frequency. Moreover, throughput of the system increases and hence enables an additional degree of freedom in controlling and managing the droplet volume.

Figure 5:
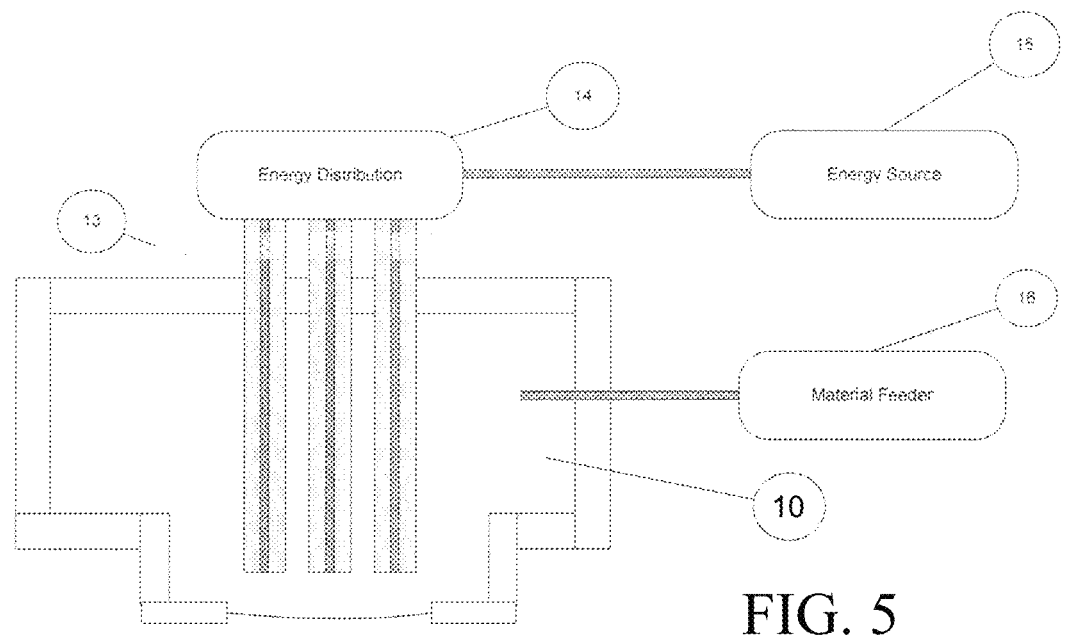
FIG. 5 schematically illustrates a non-limiting embodiment of the invention herein disclosed in which the system comprises a plurality of energy transfer means.

Reference is now made to FIG. 5, which illustrates schematically (not to scale) one reservoir in an embodiment of the system herein disclosed in which the system comprises at least one reservoir into which a plurality of energy sources or energy transfer means (e.g. a plurality of waveguides) have been introduced. In the particular embodiment illustrated in the figure, energy is transferred from a single energy source 15 such as a laser to energy distribution head 14. The energy distribution head can divide the input energy into N parts, or can distribute the energy in time, e.g. by diverting the energy sequentially to each of the energy transfer means 13. In the case in which the energy source is a laser or lasers, the energy transfer means can be a plurality of N waveguides. The energy is then transferred simultaneously or sequentially to the donor material 10. Donor material removed from the reservoir is replaced by material stored in a material feeder (16) that is in fluid connection with the reservoir.

Reference is now made to FIG. 6, illustrating a sequence of steps for an SL-LIFT process performed in the system herein disclosed according to one embodiment of the present invention. As shown in the figure, the system and method herein disclosed enable filling the reservoir without any necessity for disassembly and assembly of the apparatus of which the reservoir is a part, e.g. a printing head, or for extracting the apparatus from the location in which it has been place, e.g. in the case of a tube implanted in situ in the body of a patient or in online fluid connection with an organ of patient's body.

As shown in FIG. 6, in preferred embodiments, the reservoir opening is closed while the reservoir is being filled in order that material will not flow out of the reservoir. In preferred embodiments of the invention, the opening can be opened and closed by control of the adjustable opening mentioned above, or by manipulation of a plug or stopper (9a) connected to the waveguide. In embodiments such as the one shown in FIG. 6 in which the plug is physically attached to the waveguide, vertical motion of the waveguide will bring the plug into position to seal the reservoir opening. Additionally or alternatively, any other mechanical plug that can be electrically or vacuum controlled such as mechanical plugs, solenoids, and vacuum controllers, can be used.

In the SL-LIFT process, in contrast to standard LIFT, throughput is also derived from the refresh rate, in addition to the laser PRR and other parameters. The refresh rate is controlled by the viscosity of the material, as stated above regarding the heating; additionally or alternatively, it can be controlled by movement of the waveguide, an electric arc, or other energy transfer mechanism. Mechanical movement, such as a stirring in a lateral movement, applying ultrasonic vibration, etc., can be used to increase the refresh rate.

Reference is now made to FIG. 7, illustrating (not to scale) non-limiting embodiments of the end tip of the waveguide in which it has been treated to improve the system performance and enable additional capabilities. A local intermediate layer 18 can be provided (FIG. 7A) by any method known in the art such as coating or gluing. An intermediate layer made of material with higher thermal conductivity than that of the waveguide will improve the efficiency of the heat transfer relative to a waveguide that lacks the intermediate layer, and also enables deposition of materials that are transparent at the output wavelength of the laser.

Cleaning of the energy transfer means is essential, since residual material may accumulate on its distal end, degrading system performance. In some embodiments, coating of the end tip with hydrophobic material, or shaping of the end, is performed as a preventive measure. In some preferred embodiments, mechanical cleaning of the tip is performed, for example, by extending the tip and brushing off excess material with an automatic or semi-automatic mechanism.

In some embodiments of the invention, passive components are added to the tip of the waveguide. FIG. 7B presents a schematic illustration of a waveguide to which a lens (19) has been added. FIG. 7C presents a schematic illustration of a waveguide tip to which Graded Index (GRIN) material (19a) has been added. In other embodiments, not shown in FIG. 7, plates are added to assist focusing and to provide improved light transfer to the material. Active components as MEMS and micro mirrors can be used to scan and distribute the energy at various locations on the meniscus and in the extracted state of the waveguide can be used to pattern, ablate and sinter the printed material.

Reference is now made to FIG. 8, presenting a non-limiting schematic illustration (not to scale) of another embodiment of the SL-LIFT system disclosed in the present invention, an overall view of which is provided in FIG. 8A. In this embodiment, the system comprises a transparent rotatable cylinder (20) submerged in the reservoir; energy transfer means (e.g. a waveguide) (22) that transfers the energy to the donor material, a scanning mechanism (23), such as Galvo, MEMS, micro mirror or other scanning apparatus that directs the energy to a predetermined spot on the surface of the cylinder; and a mechanism for heating and cooling. As the cylinder rotates, it is coated with donor material, analogous to gravure printing, so that fresh material is continually presented to the energy transfer means. A close-up view of the scanning mechanism, the energy transfer means, and the rotatable cylinder presented in FIG. 8B. In this embodiment of the system, the SL-LIFT process comprises (1) coating of the cylinder with donor material by rotation in the reservoir; (2) providing an energy pulse when a coated area reaches the floor of the reservoir, thereby initiating the LIFT process; and (3) removing and recoating the cylinder with donor material as it continues to rotate.

In another embodiment of the invention, the cylindrical LIFT mechanism provides a dual technology head, serving both as an ablation patterning head and a printing head. One mode of operating said dual head is cleaning any material coating the cylinder; focusing energy on the printed substrate, which is possible because no material is coated on the cylinder; and scanning with the scanning mechanism (23) and removing or patterning according to predefined data.

Figure 9:
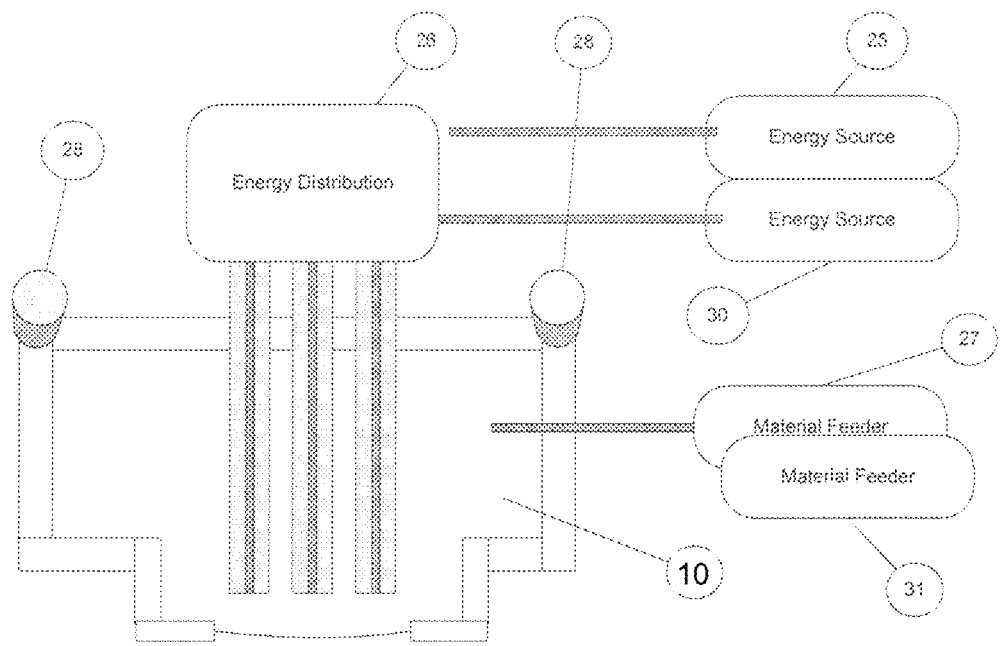
FIG. 9 schematically illustrates a non-limiting embodiment of the system herein disclosed, in which the system comprises a plurality of energy sources, a plurality of energy transfer means, a plurality of material feeders, and a mounting alignment mechanism.

Reference is now made to FIG. 9, which illustrates (not to scale) an SL-LIFT printing head comprising the rotating cylinder illustrated in FIG. 8. This printing head incorporates an advanced LIFT means, at least one first energy source (25) and at least one second energy source (30); an energy distribution mechanism (26) that is configured to receive the energy output of the energy sources and distribute it to the donor material (see FIG. 5), at least one first material feeding source (27) in fluid connection with the reservoir, at least one second material feeding source (31) in fluid connection with the reservoir, an adjustable mechanical interface (28) configured to manipulate and fix the tilt and orientation of the printing head, and a feedback mechanism to control the printing process.

Figure 10:
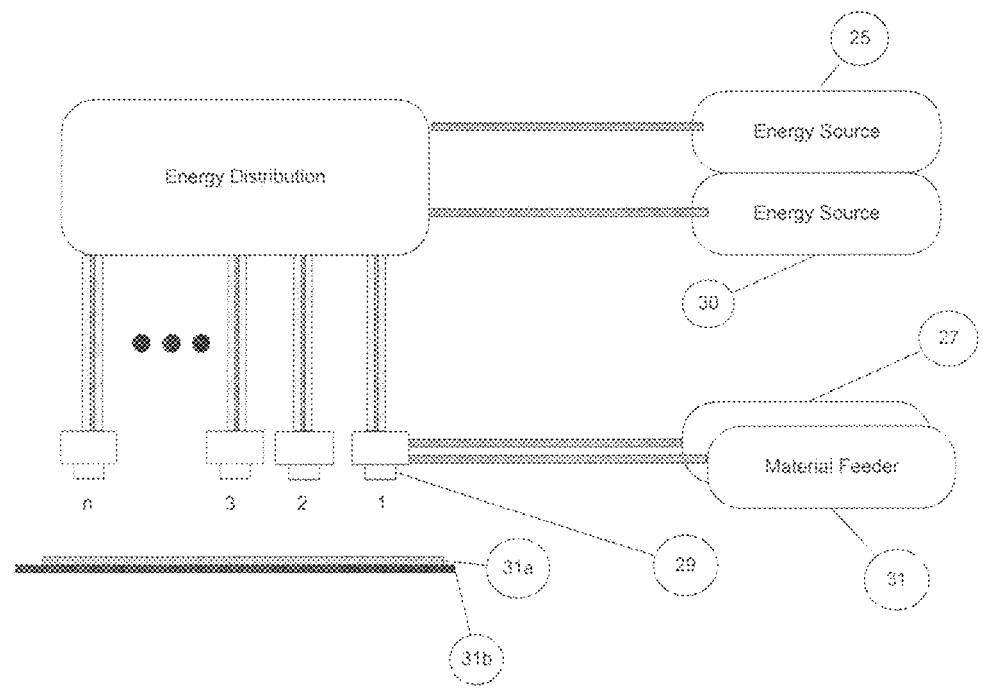
FIG. 10 schematically illustrates a system with a plurality of printing heads according to one non-limiting embodiment of the invention herein disclosed.
Figure 11A:
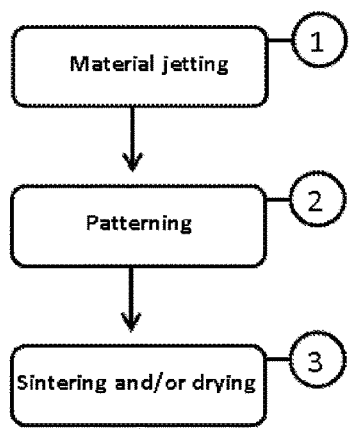
FIGS. 11A and 11B schematically illustrate a number of non-limiting exemplary basic and complex sequences, respectively, for use of the system herein disclosed.
Figure 11A:
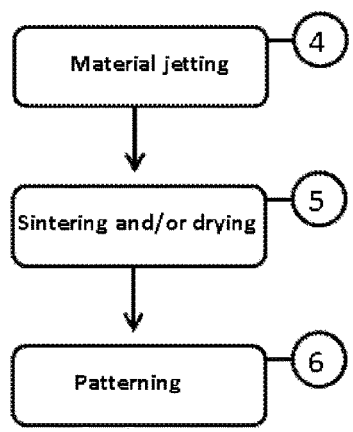
Figure 11A:
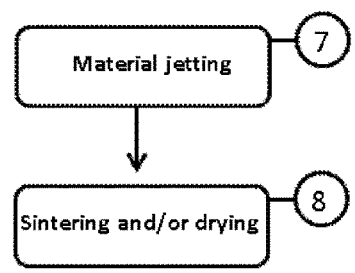
Figure 11A:
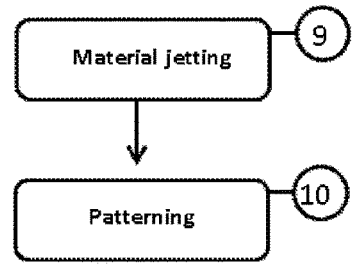
Figure 11B:
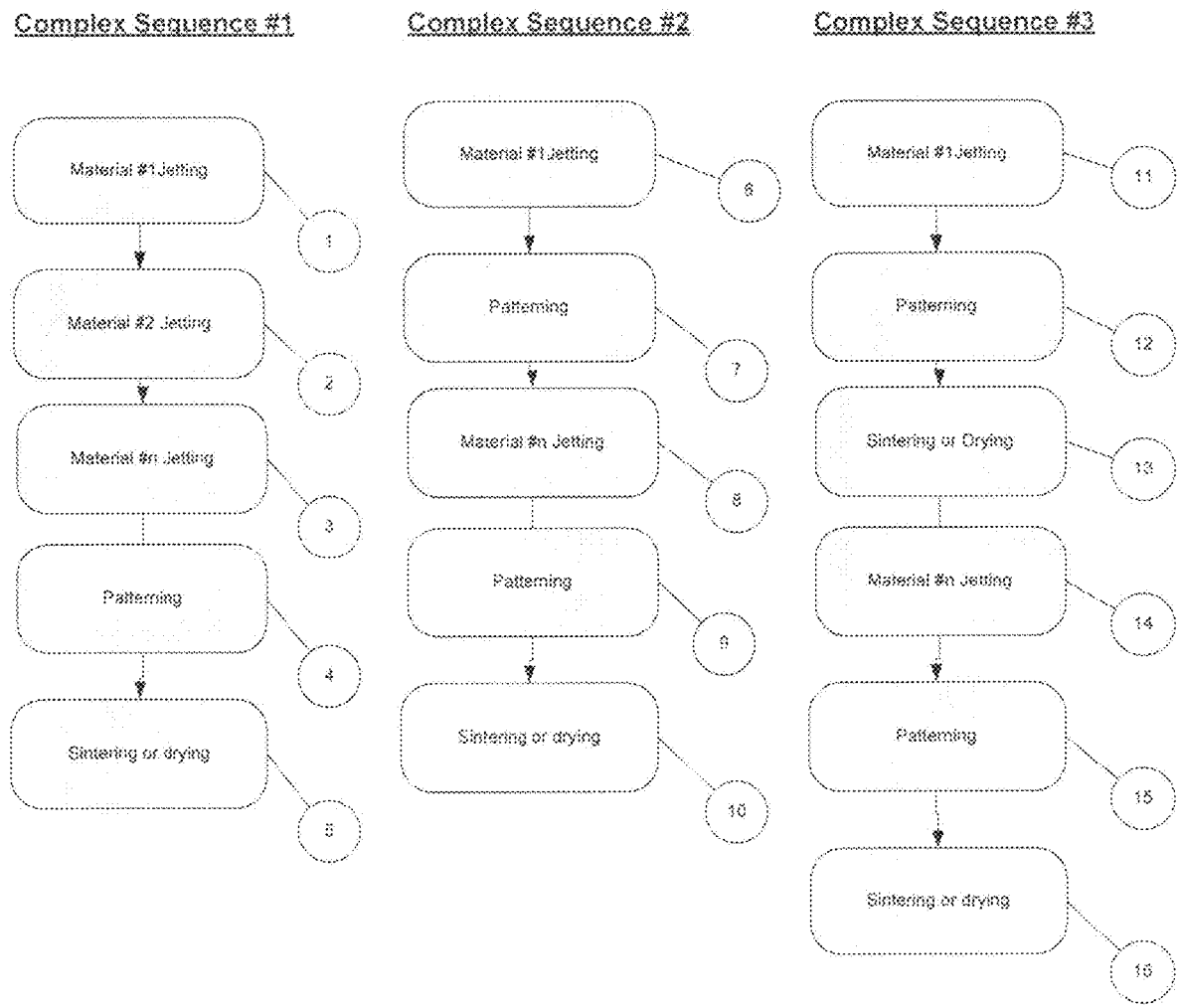

Reference is now made to FIG. 10, providing a non-limiting schematic illustration of another embodiment of a printing head according to the present invention. A plurality of N printing heads are mounted on a system and have interfaces to the energy distribution system (26), the material feeding source or sources (27), the electronics of the platform, the control mechanism of the platform and the platform software. The system interfaces are described in detail below.

One non-limiting example of a method of use of the embodiment illustrated in FIG. 10 is as follows. A printing target (31a) is mounted on an x, y, z precision stage (31b) which brings the target to a predetermined position under the printing head. As there is a plurality of independent reservoirs, each head can hold a different material. If, for example, the system is being used to produce a printed circuit, a plurality of conductive lines is printable in a predefined accurate orientation. Specific points of a non-conductive material are then printable, e.g., in an orthogonal orientation, thus providing an x-y grid of printed lines provided on one platform and by a single process. For such applications as 3D printing, N layers of up to N different materials can be printed in a single operation with or without complementary processes, such as patterning, sintering, or curing.

Material flow to the head reservoir is controlled by and supplied from the main material feeding system (27) or systems (27, 31) containing the various materials. The system controls the flow. In some embodiments of the invention, filling of the reservoir is achieved by use of stopper 9a (FIG. 2); in embodiments comprising a cylindrical head, the cylinder is moved into position to close the reservoir's opening in order to enable filling of the reservoir.

In preferred embodiments of the invention, mechanical control of the system is an integrated module of the commercially available inkjet printing heads. The orientation towards the platform is adjustable e.g., by means of a screw mechanism (28). Degrees of freedom are angles θy and θz. θx is mechanically aligned due to larger tolerances. The mechanical interface enables interface, communication, compatibility and integration with the other components of the multi technology head, the LIFT system (SL-LIFT, LD-LIFT, or other LIFT), the patterning head, the sintering head, UV curing head, thereby establishing a combined multi-technology united head. In systems where accuracy and resolution are less critical, the head is fixed to the system without the degrees of freedom for alignment.

Reference is now made to FIG. 11, which presents non-limiting examples of a number process step sequences that are possible using the apparatus illustrated in FIG. 10. Four non-limiting examples of basic sequences are illustrated in FIG. 11A. These basic sequences illustrate that unlike systems known in the art, the system of the present invention is capable of providing multiple technologies such as jetting, patterning, and sintering/drying in a single instrument rather than having to provide separate instruments for each process. Three non-limiting examples of complex sequences are illustrated in FIG. 11B. In Complex Sequence #1, N materials are jetted, followed by patterning and sintering or drying. In Complex Sequence #2, N layers of different materials are printed with complementary processes in between. A combination of these processes is illustrated by Complex Sequence #3.

Figure 12:
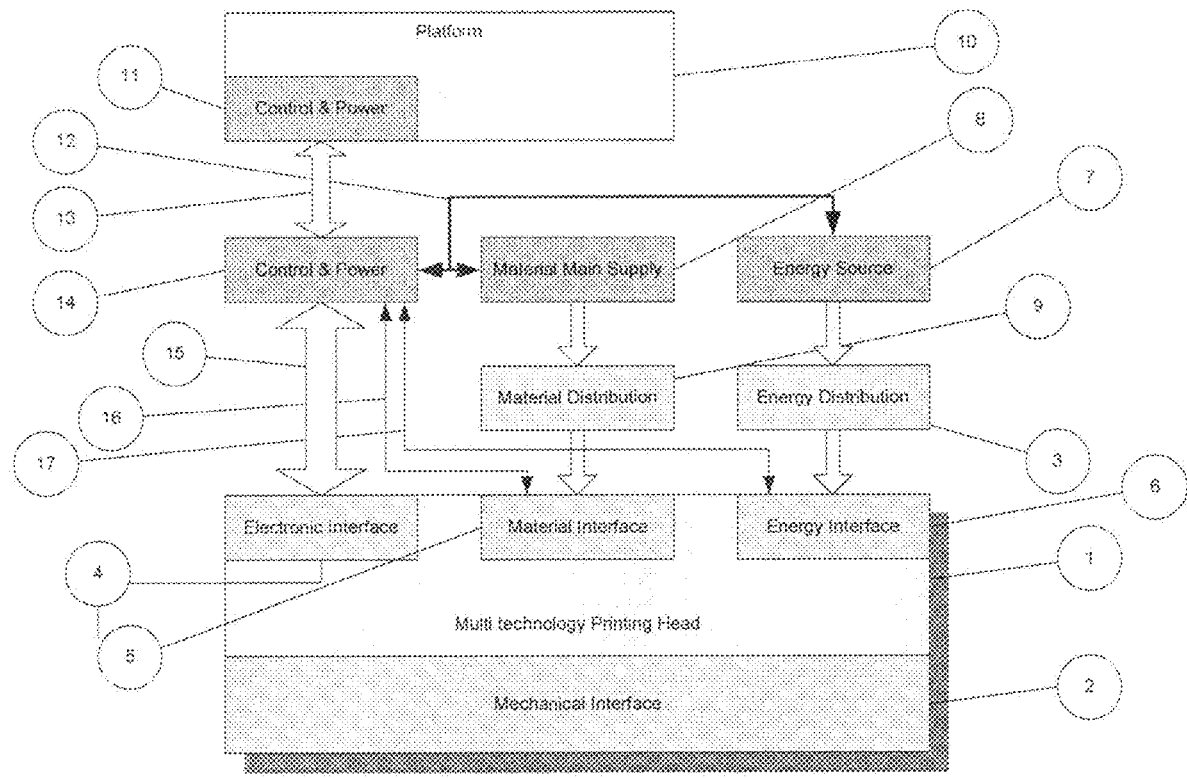
FIG. 12 schematically illustrates the control systems and interfaces of the system herein disclosed.

Reference is now made to FIG. 12, which provides a schematic illustration of the various system interfaces and control mechanisms. The control system operates according one or more of the following: data and material data provided from a feedback mechanism, predefined material information which comprises inter alia droplet size and dimensions, material types etc. The control system further adapted (i) to receive data from the feedback mechanism for the process control; and (ii) to tune droplet parameters, such as speed, power, etc. The control system can further be set to control the movement of energy sources, scanning mirrors, optics, temperature cooling and heating, timing, cleaning according to feedback etc.

The control system of the head receives pattern data and material data from the platform and transforms it to coordinates and parameters required by the printing head. Non-limiting examples of such parameters include line dimensions; locations and orientation of the lines; line height, width, length, shape and line space; the type of material being used; and parameters determining whether or not patterning, sintering, or UV curing is required. The control system is also configured to receive data from the feedback mechanism for process control the process and for tuning of printing parameters such as speed and power. Non-limiting examples of system functions that may be controlled by the control system in preferred embodiments include the movement of the energy source, movement and positioning of the scanning mirror, movement and positioning of the optics, the temperature to be provided by the heating or cooling system, timing of cleaning, and the feedback mechanism.

Material flow to the reservoir is remotely controllable; material is supplied from a main material feeding system retaining one or more materials.

The electrical interface supplies power, inter alia, to the distributing head mechanism, and controls mirrors, fibers, heating and cooling mechanisms, reservoir operation etc. The electrical interface is provided via one or more connectors and includes means for electrical control of the waveguide(s), fibers of the energy source etc.

Figure 13:
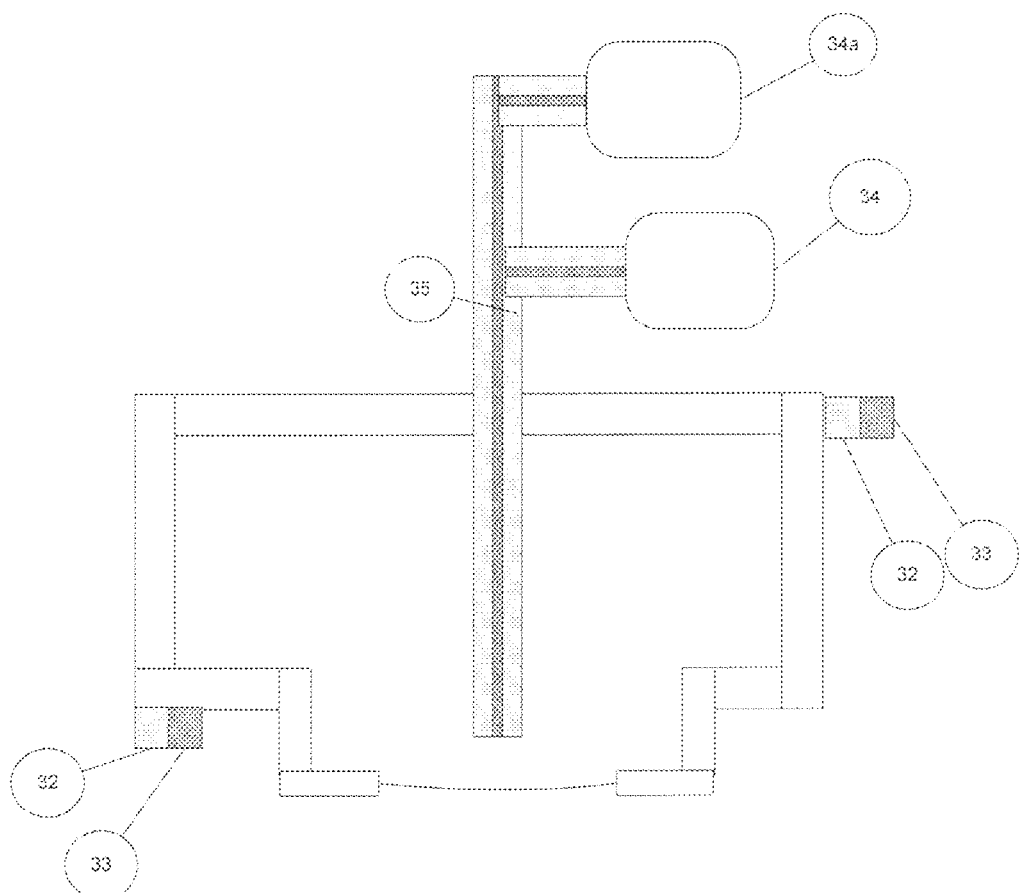
FIG. 13 schematically illustrates feedback mechanisms added on to a printing head according to one non-limiting embodiment of the invention herein disclosed.

Reference is now made to FIG. 13, which illustrates schematically (not to scale) a non-limiting embodiment of a feedback mechanism according to the present invention. In preferred embodiments, the feedback mechanism is incorporated into the printing head. A sensor array such as a CCD or CMOS (32) or any other suitable array, photo-detector, quad detector or other power detector is mounted in or on the head. In various embodiments, the feedback mechanism may be integrated with the light source 33 or waveguide 35. Additionally or alternatively, it may be mounted external to the waveguide, for example, near the energy source 34 or one or more additional energy sources 34a. In preferred embodiments of the invention, the feedback mechanism is used to calibrate and synchronize the printing head(s) and to provide process control for processes such as printing, patterning, sintering, and/or UV curing.

Figure 14:
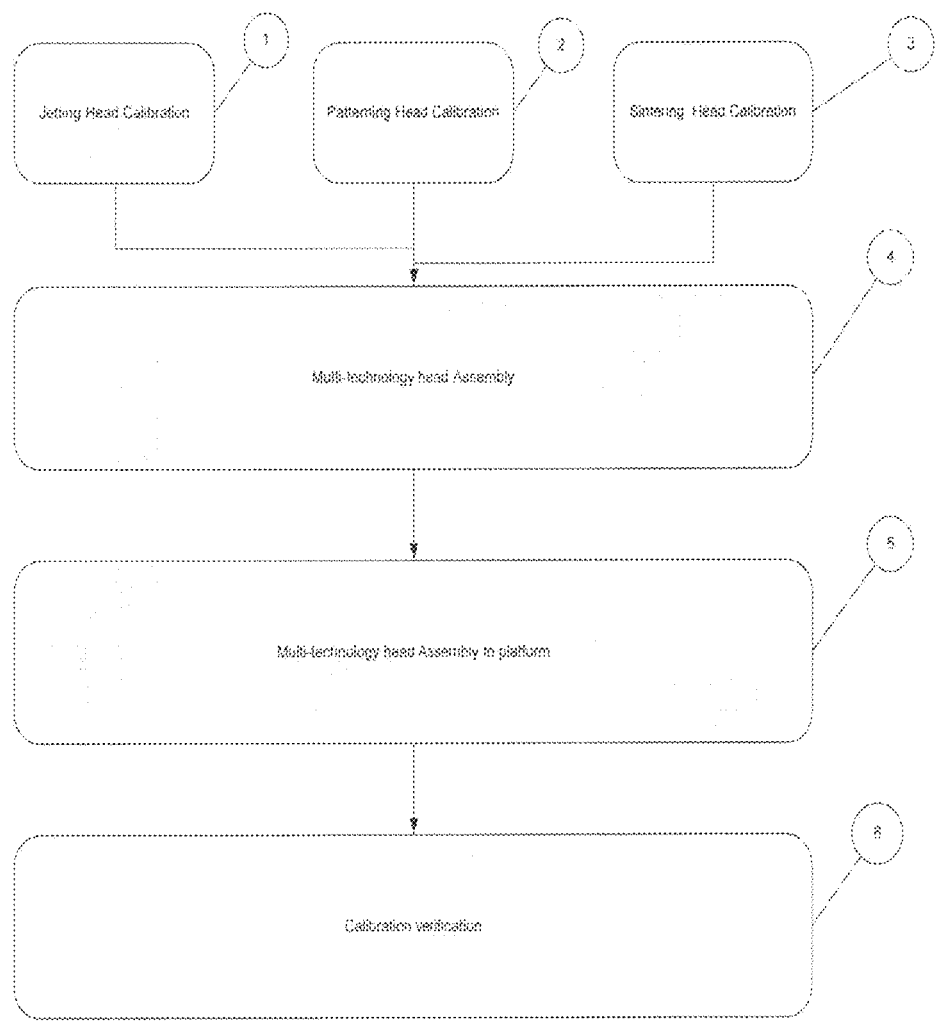
FIG. 14 schematically illustrates a calibration sequence for the system herein disclosed.

Reference is now made to FIG. 14, illustrating a non-limiting example of a calibration sequence according to one embodiment of the invention. The multiple heads are can be calibrated during assembly. The calibration is provided by calibration targets that are pre-manufactured or printed by the jetting head. The calibration is supported by the control system, electronic mechanism and software. The calibration output is saved and used by the application software. In the most preferred embodiments, each head can be calibrated independently with sufficient accuracy to support calibration of the multi-technology head. In preferred embodiments of the invention, the calibration mechanism that calibrates the printing head is based on the feedback obtained by the feedback mechanism. In the system herein disclosed, calibration and registration targets can be pre-prepared on the printed platform or printed by the jetting mechanism and acquired by the feedback mechanism by any appropriate mechanism known in the art such as a sensor array, CCD, CMOS, etc.

Figure 15:
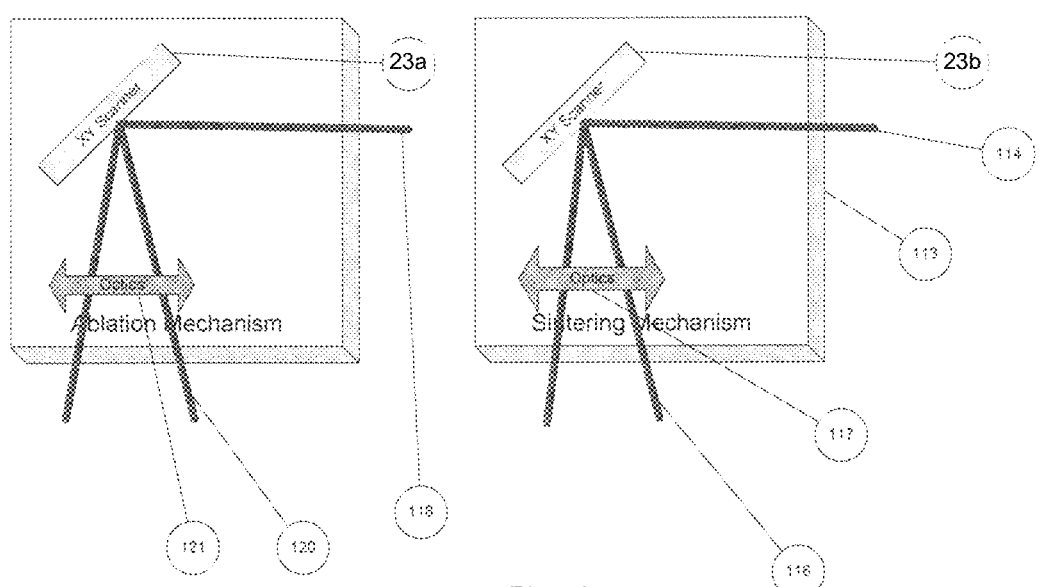
FIG. 15 schematically illustrates sintering and patterning heads according to one embodiment of the system herein disclosed.

An example of how the system disclosed in the present invention can combine into a single systems functions which, in systems known in the art, are performed by separate instruments is illustrated in FIG. 15. The figure illustrates schematically sintering and printing modules of a system according to one embodiment of the invention disclosed herein. Each module comprises an x-y scanner (23a and 23b, respectively), optics (121 and 117, respectively), an operating mechanism (120 and 116, respectively), and energy transfer means such as a waveguide (118 and 114, respectively). In the embodiment shown, both waveguides bring light to their respective module from a single laser (not shown in the figure), unlike systems known in the art, which would require two separate energy sources.

If the sintering is performed, for example, to produce a printed material, the sintering will be geometry-dependent. The method of sintering comprises steps of monitoring the printed substrate and providing feedback to the system from the results of the monitoring, thereby measuring levels of sintering of the material in real time and on-line, and defining its physical dimensions. In one embodiment of the invention, a first pass of the head measures the geometrical properties of the printed lines. Feedback R(x,y) as a function of power, and the energy source in the sintering head is initiated. The sintering power is controllable and has various wave forms; energy can be raised constantly, in a high rise time method or other wave form. In this way, sintering time and sintering quality of the printed line are optimized.

Figure 16:
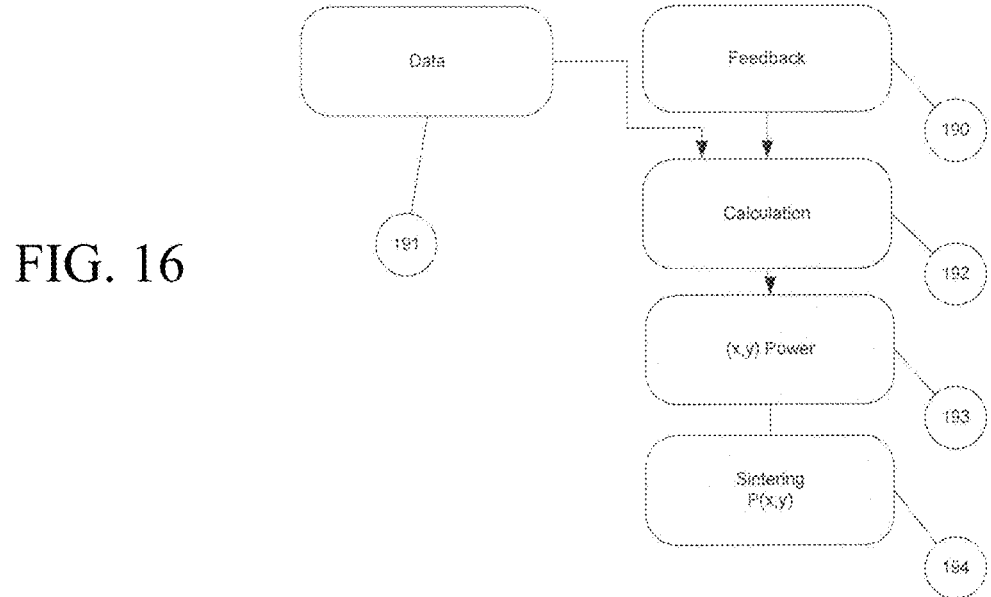
FIG. 16 schematically illustrates the steps of a sintering process according to one embodiment of the invention herein disclosed.

Reference is now made to FIG. 16, which illustrates a non-limiting embodiment of the steps of a sintering process used by the system disclosed in the present invention. Data is received from feedback mechanism 190 and from manufacturing data 191 provided to the system. The necessary system parameters are then calculated (192) from these values. From prior knowledge of the material being sintered and its dimensions, a power function P(x, y) is calculated and provided to the sintering module. The power function may also include parameters related to scanning, power, speed and other process parameters (194). Once the power function is calculated, the energy source provides power to the module, with the power supplied to the module when it is focused on any given point according to the power function.

The final form of the printed material is obtained by combining processes of jetting and patterning. The process of jetting comprises depositing the donor material on a receiver substrate. Excess material is then removed by use of the patterning head. Process steps such as ablation of excess material are then performed, for example, by pulsing energy from an energy source, a focusing and scanning it on the printed substrate. Non-limiting examples of process steps were given above (see FIG. 11).

It is known in the art that various materials and inks are cured by energy of UV wavelength. It is in the scope of the invention wherein the UV curing head is adapted to emit energy at a required predefined wavelength to cure these inks. A feedback mechanism and a previously obtained pattern data are both utilizable in emitting energy at a required location R(x,y). In preferred embodiments, the UV source is a UV diode, laser diode, UV LED, or UV lamp. Alternatively or additionally, UV light can be distributed to the various curing heads via a laser distribution mechanism (105), as discussed above.

Figures 17, 18:
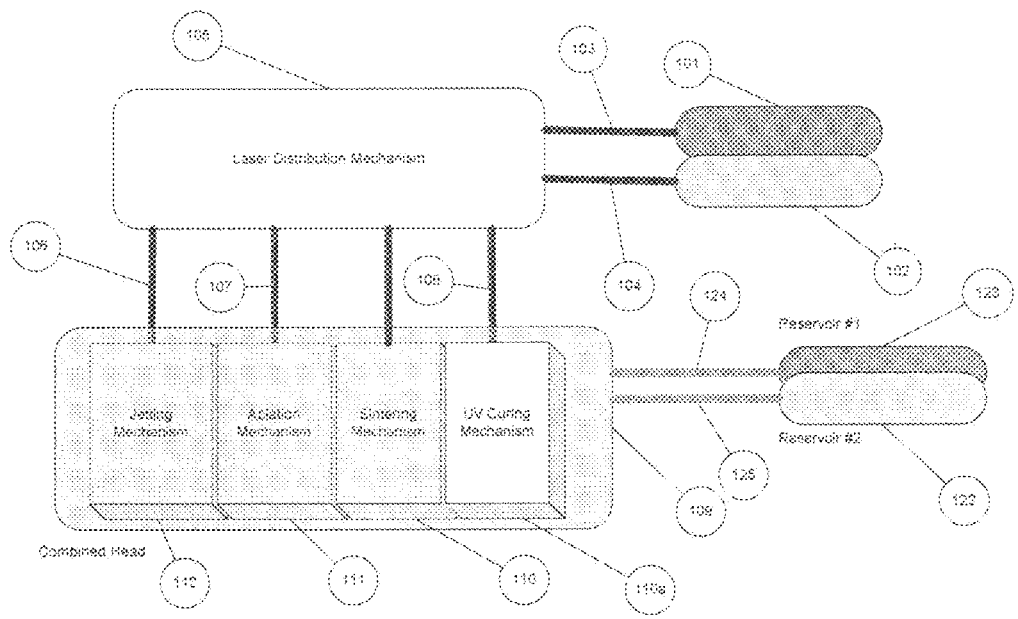
FIG. 17 schematically illustrates one embodiment of the invention herein disclosed in which a plurality of modules are combined into a single system.
FIG. 18 schematically illustrates a complete LIFT system according to one embodiment of the invention herein disclosed.

In preferred embodiments of the system herein disclosed, modules with independent functionalities are combined into a single LIFT system. Reference is now made to FIG. 17, schematically illustrating one embodiment of such a system. The system illustrated in FIG. 17 integrates four modules in a single head: a laser jetting head (112); a laser patterning head (111); a laser sintering head (110); and an UV curing head (110a).

According to one embodiment of the invention, a jetting head based on substrate-less laser induced forward transfer (SL-LIFT) comprises one or more of the following: one or more pattering heads, one or more drying heads, one or more sintering heads and one or more UV curing heads. The combined apparatus acts as a single device and interfaces the system as one integrated mechanism. The energy, material, electronics, control and other feedings to the apparatus are the same in a single and a multi-head system. It is in the scope of the invention wherein the system comprises one or more jetting heads with patterning abilities, a jetting head with sintering abilities; and a jetting head with patterning abilities and sintering head, combination with an UV curing head etc. A single or a plurality of energy sources is provided in the system according to the required application. Multiple material feeders of different substances are incorporable in the system according to a required application.

Reference is now made to FIG. 18, illustrating a non-limiting example (not to scale) of a full LIFT system according to one embodiment of the invention. The LIFT system may comprise any or all of LIFT, LD-LIFT, or SL-LIFT. The SL LIFT or LD LIFT or LIFT head prints patterns as 180, 180a and 180b, a feedback mechanism as 181, 182 and/or 176 which acquires the shapes printed on the acceptor (178). The coordinates of the shapes and their dimensions are related to a x,y location relative to the printed patterns (180, 180a,180b) and relative to the x, y stage (179). The sintering, patterning or UV curing head (171), operates according to the feedback parameters, and by controlling the laser or energy source (170) and the scanning mechanism (173) and effective sintering, patterning and curing is achieved. The source and detector of the feedback mechanism can be separated (181, 182) or integrated into a single mechanism (176).

Figure 19A:
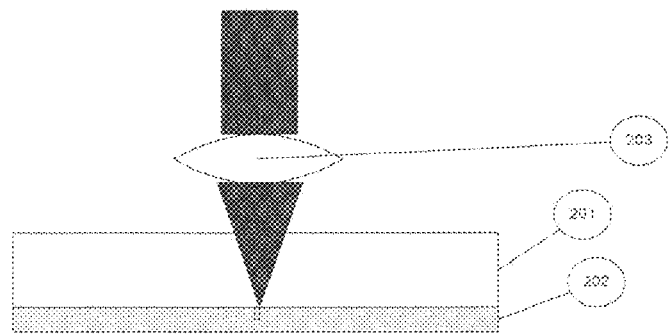
Figure 19B:
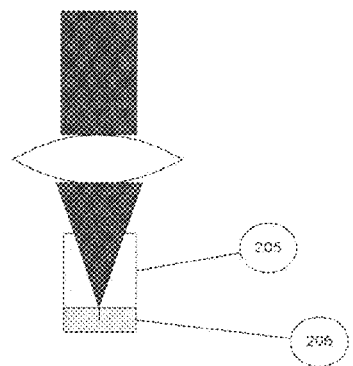

Reference is now made to FIG. 19, schematically illustrating (not to scale) the "local donor LIFT" (LD-LIFT) process of the present invention and how it contrasts with the standard LIFT process known in the prior art. The standard LIFT process described above and illustrated in FIG. 19A comprises a substrate (201), a donor material (202), and focusing elements (203). FIG. 19B illustrates schematically what in principle would happen if the substrate were reduced in size to the point where only that part of the substrate and donor material heated by the laser remained (~20 microns surrounding the laser spot). In such a case, the standard LIFT process would continue to operate since the interaction between the energy source and the material 206 that is plated or coated on the donor substrate 205, and the consequent LIFT process, will be the same as in the standard prior art LIFT setup shown in FIG. 19A.

Figure 19C:
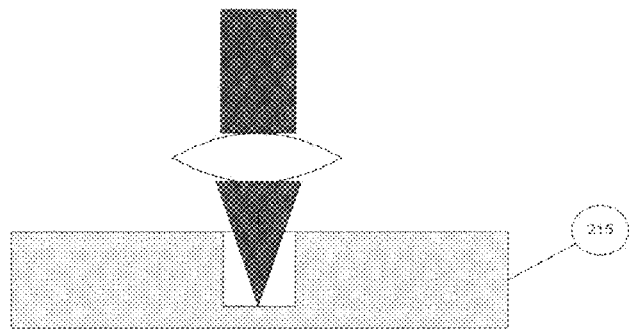

Reference is now made to FIG. 19C, which illustrates schematically one embodiment of the present invention, in which donor material 215 is embedded in or is part of the reservoir or flows through it. The fundamental physical interaction between the energy source and the donor material will thus be the same as that shown in FIG. 19B and hence the same as in the standard LIFT shown in FIG. 19A, demonstrating that a LIFT process will occur under conditions in which the material resides in or flows through the reservoir, even lacking a donor substrate. This process is referred to herein as "Local Donor LIFT" (LD-LIFT).

The invention herein disclosed incorporates introduction of the local donor or donors into a reservoir (215), which continues to support a standard LIFT mechanism, thus deriving a "local donor LIFT" method and systems thereof. Reservoir (215) may incorporate a flow of material, thereby refreshing the local donor (205) and enabling high frequency and continuous printing.

In preferred embodiments of the invention, it further comprises means for moving each waveguide along its longitudinal axis. Non-limiting examples of such means include piezoelectric, magnetic, and microelectromechanical systems (MEMS). In some embodiments of the invention, these means are configured to be able to translate the waveguide(s) entirely out of the reservoir(s).

It is in the scope of the invention wherein a system as defined in any of the above comprises a camera monitor to support registering, calibrating and monitoring of the printing, patterning and sintering process.

Figure 20:
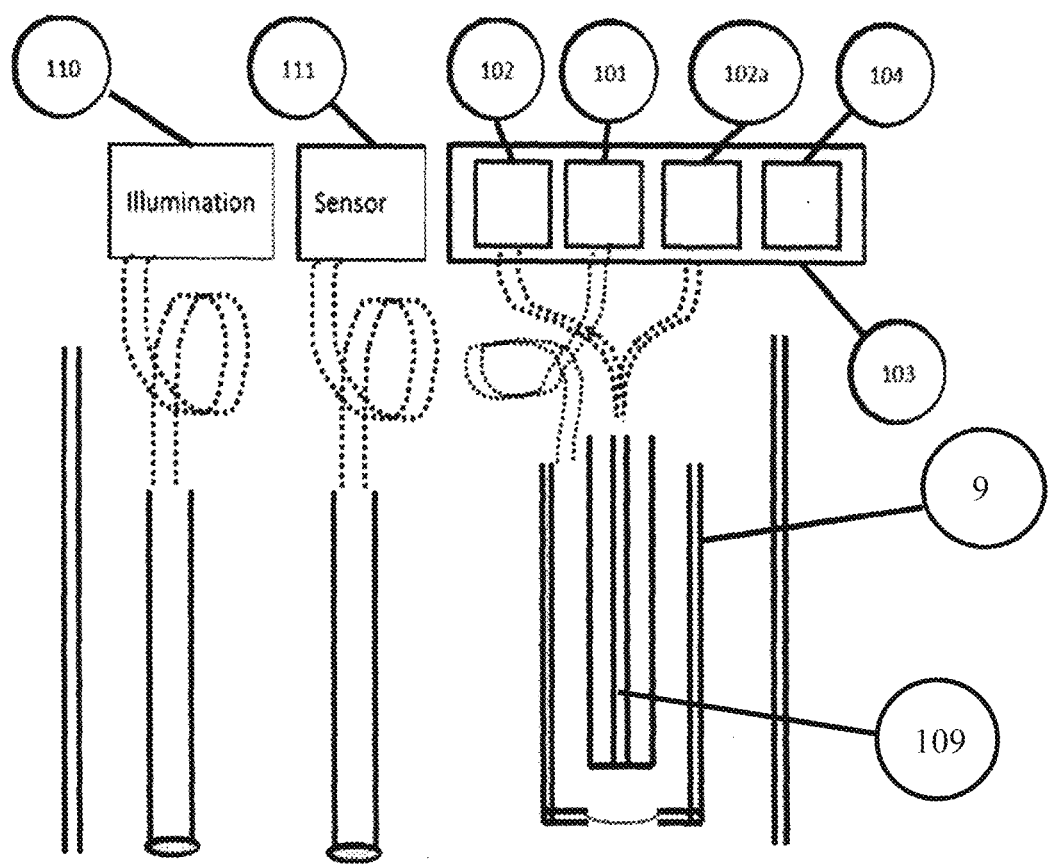

While the preceding disclosure has emphasized those embodiments of the system and methods herein disclosed that are most relevant to printing technology, production of medical devices via LD-LIFT and/or SL-LIFT is also within the scope of the invention. Reference is made now to FIG. 20, schematically illustrating a system comprising a microtube LIFT distribution mechanism, an illumination source, a feedback mechanism, all embedded or otherwise incorporated in a tubular medical device. Illumination source (110) may be selected from a LED, SLED, laser diode or any other illumination source which emits light into a fiber or a bundle of fibers, thereby and illuminating an area that the material is deposited to. This arrangement feedbacks sensor (111) to position, and provides accuracy and high yields in deposition of the material distributed by micro-tube (109). Reservoir (109) is embedded into, in fluid connection with, or otherwise incorporated to the medical device. An additional energy source (102a) functions as either feedback mechanism or a heating mechanism is transferred through the waveguide or alternatively, through an additional waveguide, and submerged in the material stored in the reservoir.

Embodiments of the LIFT printing head and device in which the printing head and device are configured for bio-printing are considered by the inventors as being within the scope of the invention. Non-limiting examples of products that can be bio-printed by the LIFT printing head an device in which they are configured for bio-printing include biological tissue, organs, micro-organs, scaffolds, biological substances, and sacrificial materials. In addition, a method of bio-printing of biological tissues and organs using the LIFT printing head and device and LIFT printing method disclosed herein are considered by the inventors as being within the scope of the invention.

The inventive bio-fabrication method is based on 2D or 3D printing of biological materials. Non-limiting examples of biological materials that can be used in the inventive system and method include bio-polymers, cells, cell culture media, soluble sacrificial materials, extra-cellular materials, growth factors, scaffolding materials, etc. As in the general system and method described above, a plurality of biological materials may be used, each of which is stored in a separate reservoir and from there flowed to the LIFT head. The biological materials are either deposited from the reservoir or flowed into the LIFT head, and then deposited on a surface to form the desired structure and shape of the bio-printed material (e.g. tissue or organ) using the system and method as described above. The high resolution of the LIFT technique allows the printing of droplets with the size of a single cell, which is necessary for the formation of small elements in the tissue, such as a vascular system, a nervous system or bile duct. After printing, the material is consolidated and stiffened. As one skilled in the art will appreciate, the particular technique for consolidation and stiffening used will depend on the particular biological structure being fabricated and the materials being used. Non-limiting examples of such techniques include irradiation (e.g. with visible or UV light), heating, addition of appropriate enzymes to initiate crosslinking, or simply by allowing the fabricated material to rest for a predetermined length of time. The fabricated material is then allowed to mature under appropriate conditions. In vivo bio-printing in which bio-printing is performed into or onto the body of a patient in need thereof is considered by the inventors to be within the scope of the invention.

As is known in the prior art, while the LIFT process does not harm the cells during printing, environmental conditions should be strictly maintained (see "3D Bioprinting of Tissues and Organs", S. V. Murphy and A. Atala, *Nat. Biotech.* 32, 2014, which is incorporated in its entirety by reference).

In some embodiments, cells are printed with the ink, and are deposited by the LIFT method in positions that will enable them to create functioning tissue. In other embodiments, only biological materials (e.g. hydrogels) and printed, and the cells are seeded afterward. In some cases, the fabrication is done by multiple printing processes of different materials or cells, or by using additional fabrication methods.

The invention claimed is:

1. A system for performing substrateless and/or local donor Laser Induced Forward Transfer (LIFT), comprising:
   a reservoir (9) comprising at least one opening; and,
   an energy source configured to deliver energy to a donor material within said reservoir and thereby initiate a LIFT process;
   wherein said system is characterized in a manner selected from the group consisting of:
   said reservoir is embedded into a medical device;
   said reservoir is in fluid connection with a medical device;
   said reservoir is incorporated into a medical device;
   said reservoir contains at least one biologically active substance; and,
   said reservoir is in fluid connection with at least one source of at least one biologically active substance,
   additionally comprising flow means for providing a continuous flow of material through said reservoir.

2. The system according to claim 1, wherein said reservoir comprises distributable material, and said system comprises:
   a. at least one tube filled with said material;
   b. a waveguide or other energy source which is submerged in the reservoir;
   c. a tube embedded in or onto said medical device; and,
   d. a pulsed laser which generates said LIFT process in said medical device.

3. The system according to claim 2, wherein said medical device comprises at least one illumination and acquisition fiber.

4. The system according to claim 1, wherein said energy source comprises at least one source selected from the group consisting of a laser; a heating filament; an electric arc; and an electronic resistance mechanism.

5. The system according to claim 4, wherein said energy source is a pulsed laser.

6. The system according to claim 1, additionally comprising energy transfer means (8) for transferring energy from said energy source to a donor material within said reservoir.

7. The system according to claim 6, wherein said energy source comprises a laser and said energy transfer means comprises a waveguide.

8. The system according to claim 7, additionally comprising a waveguide positioning system selected from the group consisting of a piezoelectric system, a magnetic system, and a microelectromechanical system (MEMS).

9. The system according to claim 7, comprising at least one additional optical element in optical communication with a light beam passing through said waveguide.

10. The system according to claim 9, wherein said additional optical element is selected from the group consisting of lenses, mirrors, filters, scanning elements, and optical coatings.

11. The system according to claim 10, wherein said optical element is disposed at a distal end of said waveguide.

12. The system according to claim 1, additionally comprising cleaning means for cleaning at least one of said waveguide and said energy source.

13. The system according to claim 1, additionally comprising temperature regulating means for regulating temperature of material within said reservoir.

14. The system according to claim 13, wherein said temperature regulating means are selected from the group consisting of an electric current passing through at least one wall of said reservoir; thermoelectric heater; thermoelectric cooler; Peltier module; irradiation by a CW laser; irradiation by a quasi-CW laser; irradiation by a pulsed laser; and heat pipes.

15. The system according to claim 1, additionally comprising surface shape controlling means for controlling a surface shape of said material.

16. The system according to claim 15, wherein said surface shape controlling means are selected from the group consisting of electro-wetting, coating, heating of a reservoir wall surrounding said opening, and any combination thereof.

17. The system according to claim 1, wherein said system comprises a plurality of energy sources.

18. The system according to claim 1, wherein said system comprises a plurality of energy transfer means.

19. The system according to claim 1, additionally comprising adjustment means for adjusting the size of said opening.

20. The system according to claim 1, additionally comprising preheating means for preheating material within said reservoir.

21. The system according to claim 20, wherein said preheating means are selected from the group consisting of CW lasers and quasi-CW lasers.

22. The system according to claim 6, additionally comprising a plurality of energy transfer means and energy distribution means for distributing output of said energy source among said plurality of energy transfer means.

23. The system according to claim 1, additionally comprising a rotatable cylinder (20) disposed within said reservoir such that said rotatable cylinder is in contact with said donor material and such that energy from said energy source is deposited on an interior surface of said rotatable cylinder.

24. The system according to claim 23, wherein said rotatable cylinder is transparent.

25. The system according to claim 23, additionally comprising a scanning mechanism (23), said scanning mechanism disposed to accept energy from said energy source to direct at least a portion of said energy to a predetermined spot on a surface of said cylinder.

26. The system according to claim 25, wherein said scanning mechanism is selected from the group consisting of Galvo, MEMS, and micro mirrors.

27. The system according to claim 23, comprising a folding and scanning mirror and focusing optics, said mirror and optics disposed within said cylinder so as to focus energy from said energy source onto a spot on a surface of said cylinder opposite to said opening.

28. The system according to claim 23, wherein said rotatable cylinder is translatable to a position that closes said opening.

29. The system according to claim 23, additionally comprising an intermediate plate of thermally conducting material is coated on said cylinder.

30. The system according to claim 1, additionally comprising at least one printing head in fluid connection with said reservoir.

31. The system according to claim 30, wherein said reservoir is disposed within said printing head.

32. The system according to claim 30, additionally comprising a local energy source in each of said printing heads, said local energy source comprising a gain mechanism.

33. The system according to claim 30, additionally comprising a distributor configured to distribute material in a method selected from the group consisting of substrateless LIFT and local donor LIFT.

34. The system according to claim 1, wherein said energy source is a pulsed laser, and additionally comprising laser parameter controlling means for controlling at least one laser parameter selected from the group consisting of pulse width, pulse repetition frequency, pulse power, and pulse shape.

35. The system according to claim 6, wherein said energy transfer means is at least partially coated with a hydrophobic coating.

36. The system according to claim 6, wherein said energy transfer means is at least partially coated with a hydrophilic coating.

37. The system according to claim 23, wherein at least one selected from the group consisting of said energy distribution means and at least one of said energy transfer means is at least partially coated with a hydrophobic coating.

38. The system according to claim 23, wherein at least one selected from the group consisting of said energy distribution means and at least one of said energy transfer means is at least partially coated with a hydrophilic coating.

39. The system according to claim 23, wherein at least one selected from the group consisting of said energy distribution means and at least one of said energy transfer means is at least partially coated with a coating, and characterized by a predetermined hydrophobicity determined by at least one factor chosen from the group consisting of extent of coating with said coating and hydrophobicity of said coating.

40. The system according to claim 6, additionally comprising an intermediate plate of thermally conductive material disposed at a distal end of said energy transfer means.

41. The system according to claim 7, wherein said waveguide additionally comprises a graded index element.

42. The system according to claim 1, additionally comprising flow means for providing a continuous flow of material through said reservoir.

43. The system according to claim 1, additionally comprising a feedback mechanism that supports at least one of calibration, synchronization, alignment, and process control of said system.

44. The system according to claim 43, wherein said feedback mechanism comprises at least one component selected from the group consisting of a sensor, array of sensors, cameras, a source and detector, and any combination thereof.

45. The system according to claim 1, additionally comprising alignment screws disposed to provide $\theta_x$, $\theta_y$, and $\theta_z$ alignment.

46. The system according to claim 1, additionally comprising a sensor that acquires a printed target that has been printed on a different system or a target printed by this system in the same session.

47. The system according to claim 1, comprising a sensor configured to measure at least one parameter of material printed by said system, and provides feedback to at least one system selected from the group consisting of process control, sintering, and curing.

48. The system according to claim 1, wherein said reservoir is constructed of a material compatible with an acidic donor material.

49. The system according to claim 1, wherein said reservoir is embedded into, in fluid connection with, or otherwise incorporated into a medical device.

50. The system according to claim 49, wherein said system is configured to be used in a treatment protocol that comprises embedding a predefined material within or onto the body of a patient in need thereof.

51. The system according to claim 50, wherein said system is configured to be utilizable without any necessity to prepare a substrate prior to distribution of said predetermined material.

52. The system according to claim 50, wherein said predefined material comprises a biologically active substance.

53. The system according to claim 49, wherein said system is configured to dispose or embed a predefined material within or onto a cell, organ, tissue, or other biological structure.

54. The system according to claim 53, wherein said system is configured to be utilizable without any necessity to prepare a substrate prior to distribution of said predetermined material.

55. The system according to claim 53, wherein said predefined material comprises a biologically active substance.

56. The system according to claim 1, wherein said reservoir contains or is in fluid connection with at least one source of at least one biologically active substance.

57. The system according to claim 1, wherein said system comprises a micro-tube LIFT distribution system, an illumination source (110) configured to emit light into a fiber or a fiber bundle and to illuminate an area to which material is to be deposited by said LIFT process, and a feedback mechanism comprising at least one sensor (111), all of which are embedded or otherwise incorporated into said medical device; further wherein said medical device is a tubular medical device comprising a micro-tube (109) disposed so as to distribute material transferred from said reservoir by said LIFT process.

58. The system according to claim 57, comprising:
a. an additional energy source (102a) configured to function as a feedback mechanism or a heating mechanism;
b. a waveguide, one end of which is submerged in material stored in said reservoir disposed so as to transfer energy from said additional energy source to said material stored in said reservoir.

59. The system according to claim 57, wherein said illumination source (110) is selected from the group consisting of LED, SLED, and laser diode.

60. The system according to claim 1, configured for bio-printing of material selected from the group consisting of biological tissue, organs, micro-organs, scaffolds, biological substances, and sacrificial materials.

61. The system according to claim 60, configured for bio-printing of material selected from the group consisting of biological tissue, organs, micro-organs, scaffolds, biological substances, and sacrificial materials.

* * * * *